United States Patent [19]
Rexroth

[11] Patent Number: 5,632,759
[45] Date of Patent: *May 27, 1997

[54] CUTTING BLADE ASSEMBLY FOR AN ARTHROSCOPIC SURGICAL INSTRUMENT DRIVE SYSTEM

[75] Inventor: Fred Rexroth, Dunedin, Fla.

[73] Assignee: Linvatec Corporation, Largo, Fla.

[ * ] Notice: The term of this patent shall not extend beyond the expiration date of Pat. No. 5,269,794.

[21] Appl. No.: 118,851

[22] Filed: Sep. 10, 1993

Related U.S. Application Data

[60] Continuation of Ser. No. 437,270, Dec. 4, 1989, Pat. No. 5,269,794, which is a division of Ser. No. 16,140, Feb. 18, 1987, Pat. No. 5,217,478.

[51] Int. Cl.$^6$ .................. A61B 17/32; A61B 17/36
[52] U.S. Cl. .................. 606/180; 606/170; 606/167; 606/80
[58] Field of Search .................. 606/167–172, 606/174–180, 79.8

[56] References Cited

U.S. PATENT DOCUMENTS

| | | |
|---|---|---|
| Re. 30,923 | 5/1982 | Durkee . |
| 1,201,365 | 10/1916 | Shelton . |
| 1,977,263 | 10/1934 | Campbell . |
| 2,637,824 | 5/1953 | Kessel . |
| 2,754,464 | 7/1956 | Wizenez et al. . |
| 3,346,958 | 10/1967 | Sinatra et al. . |
| 3,427,720 | 2/1969 | Berman et al. . |
| 3,673,357 | 6/1972 | Molchan . |
| 3,699,294 | 10/1972 | Sudduth . |
| 3,734,099 | 5/1973 | Bender et al. . |
| 3,749,098 | 7/1973 | De Bennetot . |
| 3,817,237 | 6/1974 | Bolduc . |
| 3,848,336 | 11/1974 | Copeland . |
| 3,921,298 | 11/1975 | Fattaleh . |
| 3,924,631 | 12/1975 | Mancusi, Jr. . |
| 3,959,883 | 6/1976 | Walls et al. . |
| 4,066,851 | 1/1978 | White et al. . |
| 4,066,855 | 1/1978 | Zenk . |
| 4,104,728 | 8/1978 | Kasubuchi . |
| 4,128,889 | 12/1978 | Ojima et al. . |
| 4,216,968 | 8/1980 | Yeeda . |
| 4,220,815 | 9/1980 | Gibson et al. . |
| 4,274,407 | 6/1981 | Scarlett . |
| 4,274,414 | 6/1981 | Johnson et al. . |
| 4,276,024 | 6/1981 | Warrin . |
| 4,320,716 | 3/1982 | Haddad . |
| 4,320,767 | 3/1982 | Villa-Real . |
| 4,321,441 | 3/1982 | Thornburg . |
| 4,360,716 | 11/1982 | Fiorella . |
| 4,424,030 | 1/1984 | Smiley et al. . |
| 4,449,023 | 5/1984 | Hilhorst et al. . |
| 4,470,414 | 9/1984 | Imagawa et al. . |
| 4,593,681 | 6/1986 | Soni . |
| 4,608,215 | 8/1986 | Gonczy et al. . |

(List continued on next page.)

FOREIGN PATENT DOCUMENTS

| | | |
|---|---|---|
| 2304955 | 10/1976 | France . |
| 1036465 | 8/1958 | Germany . |
| 1192365 | 5/1965 | Germany . |
| 2712734 | 9/1978 | Germany . |
| 2840623 | 5/1979 | Germany . |
| 3122062 | 2/1982 | Germany . |
| 373518 | 1/1964 | Switzerland . |
| 2078006 | 12/1981 | United Kingdom . |
| 2093353 | 9/1982 | United Kingdom . |

OTHER PUBLICATIONS

Dentsply–Cavitron litturature: "Powermatic™ Ultrasonic Dental Unit", 1976.

*Primary Examiner*—David M. Shay

[57] ABSTRACT

A disposable cutting blade assembly for use with a handpiece having a motor for rotatably driving the cutting blade assembly includes a plastic hub mounted on a proximal end of an outer member. The hub is configured to be received in a bore in the handpiece in a particular orientation relative to blade coding sensors therein. The presence and absence of elements in the hub are detected by the sensors to identify the type of cutting blade received in the handpiece.

24 Claims, 3 Drawing Sheets

U.S. PATENT DOCUMENTS

| | | |
|---|---|---|
| 4,611,601 | 9/1986 | Bowman . |
| 4,702,738 | 10/1987 | Spencer . |
| 4,705,038 | 11/1987 | Sjostrom et al. ................. 606/180 |
| 4,737,214 | 4/1988 | Leurink et al. . |
| 4,817,607 | 4/1989 | Tatge . |
| 5,269,794 | 12/1993 | Rexroth ................................. 606/180 |

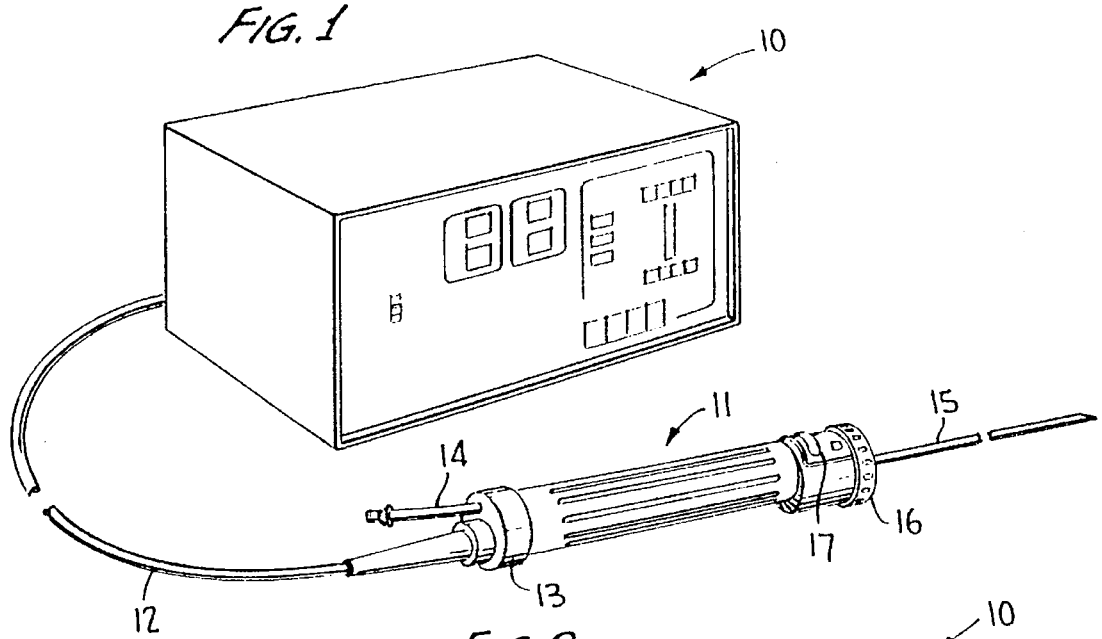
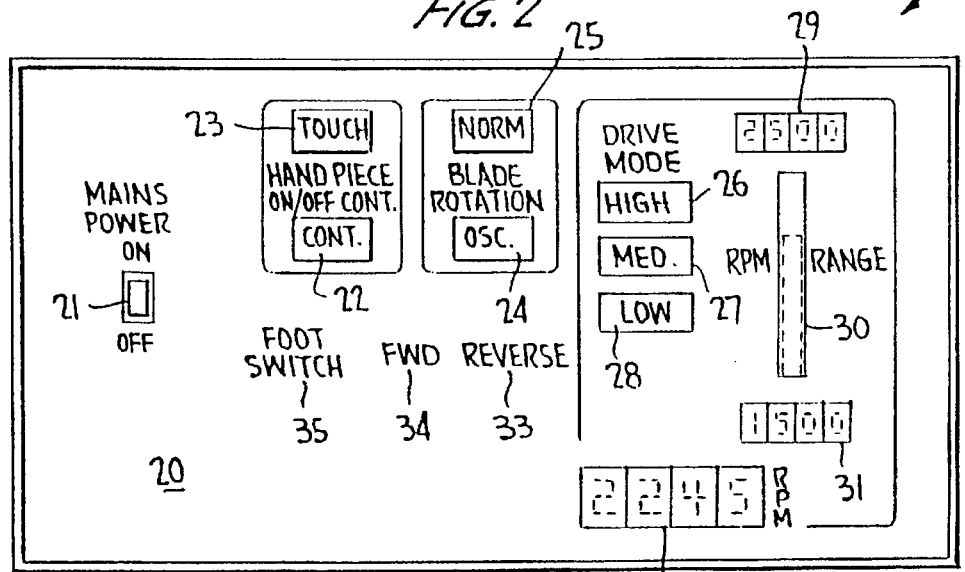
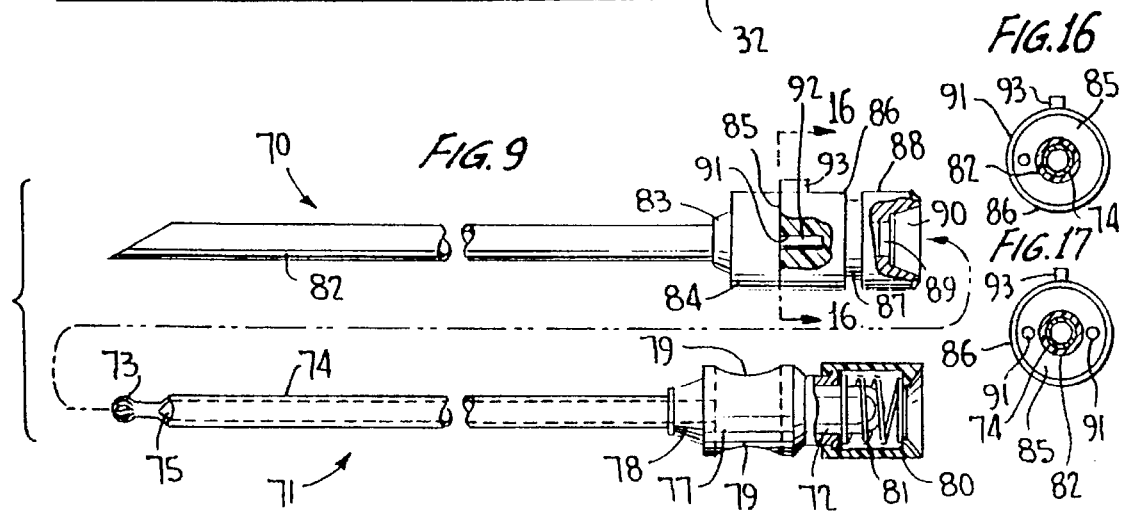

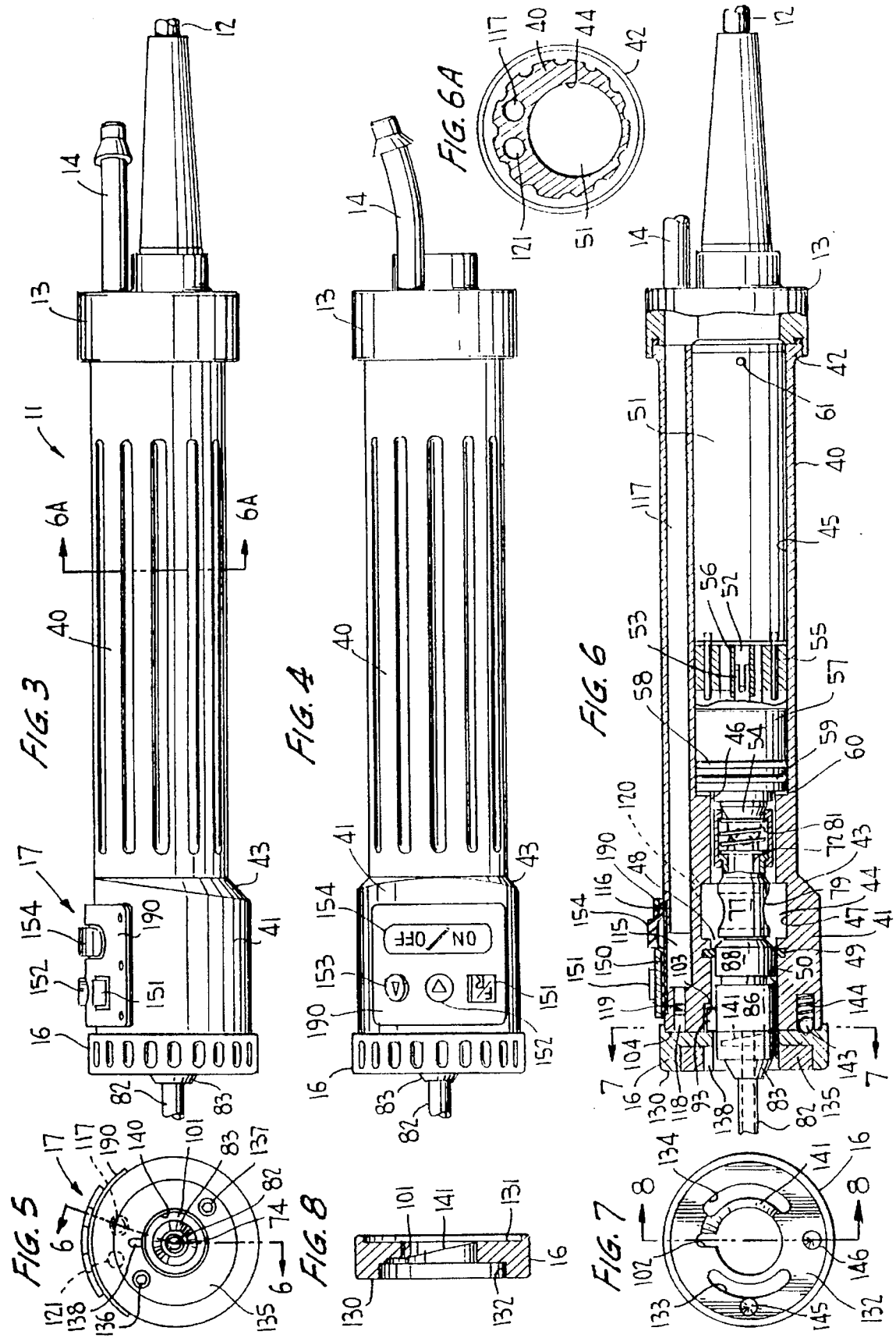

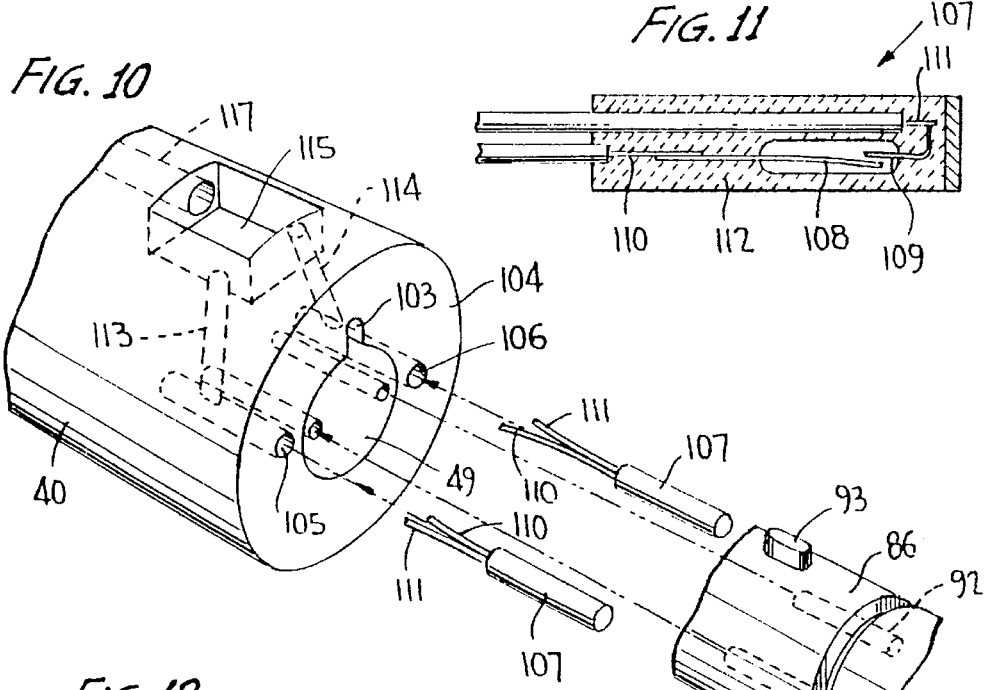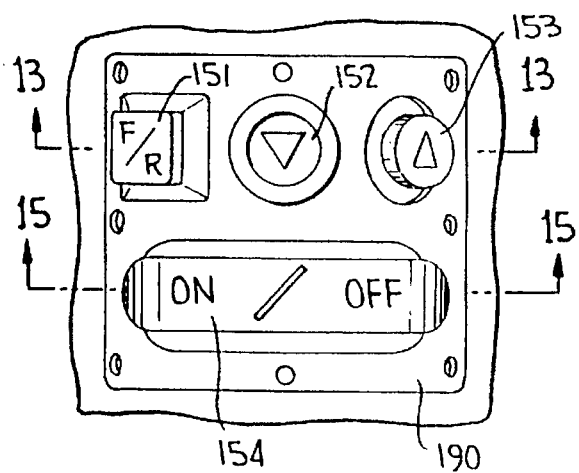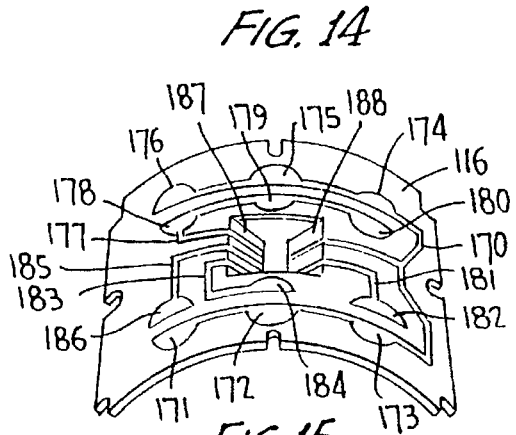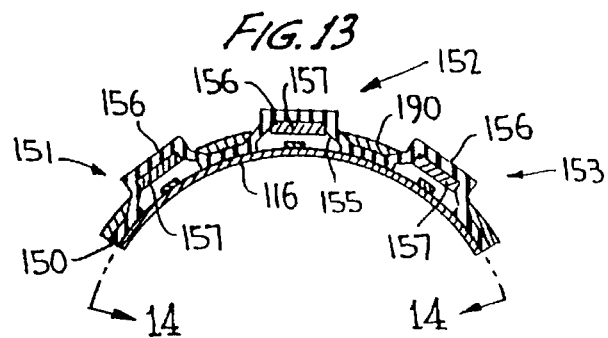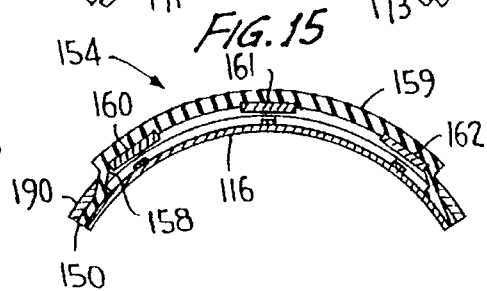

CUTTING BLADE ASSEMBLY FOR AN ARTHROSCOPIC SURGICAL INSTRUMENT DRIVE SYSTEM

This application is a continuation of application Ser. No. 07/437,270 filed Dec. 4, 1989, now U.S. Pat. No. 5,269,794 which is a division of application Ser. No. 07/016,140, filed Feb. 18, 1987, now U.S. Pat. No. 5,217,478. The entire disclosures from those applications are incorporated herein by reference.

BACKGROUND OF THE INVENTION

1. Technical Field

The present invention relates to surgical instruments and, more particularly, to instruments having rotatable motor-driven arthroscopic cutting blades capable of removing fibrous tissue lying between articulate surfaces in and around joints of the body. In addition, the instrument of the present invention can be used to balance meniscal rims and to evacuate excised tissue.

2. Discussion of the Prior Art

A typical prior art arthroscopic surgical instrument is disclosed in U.S. Pat. Nos. 4,203,444 (Bonnell et al) and 4,274,414 (Johnson et al). The disclosed instruments are elongated handpieces serving as a housing for a motor which rotatably drives a cutting blade projecting longitudinally from the forward end of the handpiece. The blade is disposed in an apertured sheath or outer tube through which excised tissue material is aspirated via suction applied through the handpiece. Controls for the motor (i.e., on/off, speed control, etc.) are located at a console and connected to the motor via a cable interconnecting the console with the handpiece.

Surgical instruments of the type described must be fabricated of material capable of withstanding autoclave temperatures (i.e., in excess of 270 degrees Fahrenheit) so that the instrument may be sterilized between surgical procedures. It is recognized in the prior art that cutting blades may be designed to be disposable (i.e., the blades are used for a single procedure and then discarded) so as to avoid the requirement of blade sterilization between procedures. However, the handpiece and the components housed therein must be repeatedly sterilized. On the other hand, the control console, which houses electrical circuitry and controls, is not required to be sterilized between uses. As a consequence, a surgeon cannot operate the console controls during a surgical procedure and must rely on an assistant to do so.

It is also recognized in the prior art that certain cutting blades, designed for specific types of surgical procedures, operate optimally within specified ranges of rotational speed. In some commercially-available systems a switch is provided on the control console to permit the operator to select a speed range that is consistent with the cutting blade to be used. A further control at the console permits the operator to select the desired speed within the selected range. A more recent development (made commercially available by Dyonics, Inc., of Andover, Mass. as the "Advanced Arthroscopic Surgical System") automatically sets the speed range appropriate for the selected cutting blade. This is achieved by providing three different cutting blade adapters (i.e., one adapter for each of the possible speed ranges) by which the cutting blade may be operably engaged with the handpiece. The adapters are coded for the desired speed range by means of one or more magnets at specified locations in the adapters. Reed switches in the handpiece are actuated by respective magnets and transmit the speed range control code information to the console to establish the correct speed range. A manual control at the console permits selection of particular speeds within the established range.

As noted above, prior art instruments of the type described have controls at the console which cannot be operated by the surgeon during a procedure without compromising sterilization. It is desirable, therefore, to provide all of the controls on the handpiece. However, there are a number of obstacles which have precluded placing the controls on the handpiece. Specifically, the entire handpiece must be capable of withstanding the temperatures experienced in an autoclave during sterilization In addition, the controls should not increase the bulk of the handpiece, particularly in its transverse dimension, since increased bulk renders the handpiece unwieldy to manipulate during surgical procedures. Finally, the controls must be located in a convenient manner so as to permit the surgeon to quickly and easily operate each control, preferably with the one hand that holds the handpiece. Prior to the present invention, the prior art has been unable to overcome this combination of obstacles.

In addition, although it is desirable to provide for automatic setting of speed ranges to optimize specific blade operation, the prior art approach has certain disadvantages. In particular, the coded adapter is an additional part of the system which must be capable of withstanding autoclaving temperatures. Consequently, the adapter is relatively heavy and adds significantly to the overall weight of the handpiece. This adversely affects manipulability of the handpiece during surgical procedures. It is desirable, therefore, to provide for automatic speed range selection while eliminating the extra adapter part.

OBJECTS AND SUMMARY OF THE INVENTION

It is therefore an object of the present invention to provide a surgical instrument of the type described wherein controls are provided at the handpiece to permit the entire operation of the instrument to be controlled from the handpiece without adding significant weight or volume to the handpiece.

It is another object of the present invention to provide a surgical instrument of the type described which includes automatic speed range selection without requiring a separate adapter part for connecting the cutting blade to the handpiece.

A further object of the invention is to provide a disposable cutting blade for a surgical instrument of the type described, which blade can be used with both the handpiece of the present invention and with the above-described prior art instruments having speed range adapters for connecting the blade to the handpiece.

It is yet another object of the present invention to provide a switch cluster on a handpiece of an arthroscopic surgical instrument wherein the cluster does not project transversely significantly beyond the contour of the handpiece, wherein the individual switches in the cluster are oriented to be easily accessed by the surgeon's hand in which the handpiece is held, and wherein the switch cluster and associated circuit in the handpiece are capable of withstanding autoclave temperatures.

A still further object of the present invention is to provide a surgical instrument of the type described wherein automatic setting of the optimal speed range for each disposable cutting blade is achieved by coding the disposable cutting blades themselves rather than by employing a separate coded and reusable adapter part for connecting the cutting blade to the handpiece.

In accordance with the present invention an arthroscopic surgical instrument can be controlled from a switch cluster located proximate the forward end of a handpiece. The switch cluster includes a plurality of pushbutton switches and is arrayed arcuately to correspond to the curvature of the handpiece periphery. An arcuate printed circuit board is disposed within the handpiece and closely spaced from the switch cluster so that actuation of each switch bridges a corresponding pair of printed circuit contacts. Both the arcuate switch cluster and the arcuate printed circuit board are constructed to withstand autoclave temperatures to which the entire handpiece assembly is subjected when sterilized. Importantly, the small radius of curvature required for the printed circuit board renders the choice of material of paramount importance in order to prevent the board from becoming brittle when exposed to autoclaving temperatures.

The switch cluster includes four pushbuttons for: (1) controlling motor direction; (2) increasing motor speed; (3) decreasing motor speed; and (4) actuating and deactuating the motor (i.e., on/off). In the optimum arrangement, switches (1), (2) and (3) are disposed proximate the forward end of the handpiece and are aligned along an arcuate path extending along the handpiece circumference. The on/off switch (4) is disposed immediately longitudinally behind the other three switches and is elongated arcuately. The surgeon can actuate each of the switches using a single finger of the hand in which the handpiece is supported. The arcuately elongated on/off switch permits the motor to be rapidly deactuated with minimal movement of the surgeon's actuation finger.

In order to automatically select the optimal motor speed range for each cutting blade, mutually interactive coding and decoding elements are disposed directly in the cutting blade and the handpiece, respectively. In the preferred embodiment, magnets are disposed in the cutting blade and reed switches are disposed in the handpiece to effect automatic speed range control in a manner similar to the prior art described above; however, and importantly, control is effected without the need for an extra adapter part. An advantage of the magnet and reed switch arrangement is that it permits the cutting blades to be usable with the handpiece of the present invention while also mechanically fitting into the adapter of the prior art handpiece. However, other cutting blade-handpiece coding arrangements may be employed, such as: mechanical projections on the cutting blade hubs positioned to actuate respective pressure-sealed switches in the handpiece; projections on the blade hubs blocking respective light paths in light-actuated circuits in the handpiece; etc. Whichever coding arrangement is used, the sensing components in the handpiece must be sealed so as not to be damaged during autoclaving.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a view in perspective of a control console and handpiece unit of a preferred embodiment of the present invention;

FIG. 2 is a view in elevation of the front panel of the control console of FIG. 1;

FIG. 3 is a side view in elevation of the handpiece unit of FIG. 1;

FIG. 4 is a top view in plan of the handpiece unit of FIG. 3;

FIG. 5 is an end view in elevation of the handpiece unit of FIG. 3;

FIG. 6 is a view in longitudinal section taken along lines 6—6 of FIG. 5;

FIG. 6A is a view in transverse section taken along lines FIG. 6A—6A of FIG. 3;

FIG. 7 is a view of the rearward-facing surface of the locking ring secured to the handpiece unit as viewed along lines 7—7 of FIG. 6;

FIG. 8 is a view in section of the locking ring taken along lines 8—8 of FIG. 7;

FIG. 9 is an exploded side view in elevation and partial section of a cutting blade assembly employed in conjunction with the handpiece unit of FIG. 6;

FIG. 10 is a diagramatic illustration of the manner in which the speed range coding of a cutting blade is detected by the handpiece unit in accordance with the principles of the present invention;

FIG. 11 is a view in longitudinal section of a reed switch employed in the handpiece unit to detect magnetic speed range coding present in cutting blade assemblies inserted into the handpiece;

FIG. 12 is a top view in plan of the control switch cluster provided on the handpiece unit of the present invention;

FIG. 13 is a view in transverse section taken along lines 13—13 of FIG. 12 and showing three of the control switches provided as part of the control switch cluster;

FIG. 14 is a view in perspective of the printed circuit board employed as part of the switch cluster assembly in the handpiece;

FIG. 15 is a view in transverse section taken along lines 15—15 of FIG. 12 and showing a fourth switch provided as part of the handpiece switch cluster;

FIG. 16 is a view in section of the cutting blade assembly taken along lines 16—16 of FIG. 9;

FIG. 17 is a view similar to that of FIG. 16 for a different cutting blade assembly coded to have a different optimal operating speed than the cutting blade assembly illustrated in FIG. 16;

DESCRIPTION OF THE PREFERRED EMBODIMENT

Referring specifically to FIG. 1 of the accompanying drawings, a surgical instrument constructed according to the present invention includes a control console 10 electrically interconnected to a surgical handpiece 11 via a flexible drive unit cable 12. Cable 12 terminates at one end in a plural-conductor connector (not shown) that is received in a receptacle (not shown) secured at the rear or side of console 10. The other end of cable 12 terminates in an end cap 13 located at the proximal or rearward end of the handpiece 11. Also extending from the handpiece end cap 13 is a suction tube 14 that communicates with the handpiece interior and serves, in a conventional manner, to conduct fluid from the handpiece to a vacuum source (not shown). Typically, a control valve is disposed in the suction line intermediate tube 14 and the vacuum source to provide control over the aspiration of fluid from the surgical site and through the handpiece interior. A cutting blade 15 projects from a locking ring 16 disposed at the forward or distal end of the handpiece 11. The handpiece is generally cylindrical and the cutting blade is oriented to project substantially coaxially along the central longitudinal axis of the locking ring 16. A cluster 17 of control switches is disposed in an arcuate array proximate the forward end of the handpiece 11, the cluster being curved to correspond to the circumferential profile of the handpiece.

As illustrated in greater detail in FIG. 2, control console 10 has a front panel 20 with a number of controls and indicators. Specifically, a mains power switch 21 of the rocker type permits application and removal of primary power to and from the system. Lighted switches 22 and 23 actuate the blade drive motor in the handpiece 11. If the continuous switch 22 is pressed and released, the drive motor rotates and the switch lights; if the switch is pressed and released again, the motor stops and the switch light is turned off. If the touch switch 23 is held depressed, the motor rotates and the switch lights; release of the switch stops the motor and turns off the switch light.

The blade rotation switches 24 and 25 control the rotation direction of the motor. When the OSC switch 24 is pressed and released, the motor changes rotation directions at pre-set intervals and the switch is lighted; the NORM switch 25 is unlighted. When the NORM switch 25 is pressed and released, the motor rotates in the direction selected at switch cluster 17 in the handpiece (as described below) and the switch is lighted; the OSC switch 26 remains unlighted.

The drive mode indicators 26, 27 and 28 are lighted to indicate when a respective motor speed range has been automatically established by the particular cutting blade 15 inserted into the handpiece (in the manner described below). The high indicator 26 lights when a high speed burr blade is inserted into the handpiece. The medium indicator 27 lights when a medium speed blade is inserted into the handpiece. The low indicator 26 lights when no blade or a low speed blade is inserted into the handpiece. In the preferred embodiment disclosed herein, the high speed range extends between 1500 and 2500 rpm; the medium range extends between 500 and 900 rpm; and the low speed range extends between 75 and 400 rpm. Indicators 26, 27 and 28 are preferably bordered in different colors corresponding to the color of the blade resulting in the automatic selection of the indicated range.

The maximum speed display 29 is a four-digit light-emitting diode (LED) display for the upper limit of the speed range currently in force. The minimum speed display 31 is a four-digit LED display for the lower limit of the speed range currently in force. The RPM range LED bar display 30 indicates the relative motor speed between the displayed minimum and maximum limits and is in the form of a lighted bar having a vertical dimension which increases with increasing motor speed. The maximum and minimum displays 29 and 31 are vertically spaced, and the range display 30 is disposed therebetween to present the range indication in a position permitting an observer to easily estimate, from the bar display, the location of the actual speed within the selected operating range. An RPM digital display 32 is a four-digit LED display of the actual motor speed. It must be noted that the word "actual" employed above to describe the speed display on bar display 30 and by digital display 32 is a misnomer. The information from which these displays are derived is the control input information originating at the console 10 and applied, by electrical signal, to the motor in the handpiece 11. In other words, the display does not reflect the measured rotational speed of the motor. However, the response of the motor to the control signal is known with sufficient accuracy to permit the control information to serve as the source of the motor speed display within the precision requirements of the system.

Indicators 33, 34 and 35 are individually illuminated status indicators. The reverse indicator 33 is illuminated when the reverse motor direction is selected at switch cluster 17 at handpiece 11; this indicator flashes on and off when the motor is rotating in reverse direction. The forward indicator 34 is illuminated when the forward motor direction is selected at switch cluster 17; this indicator also flashes when the motor is rotating in the forward direction. The footswitch indicator is illuminated when a separate foot-controlled switch (not shown) is connected to console 10. When the footswitch is so connected, the on/off, forward and reverse control switches at switch cluster 17 at the handpiece are inhibited.

Handpiece 11 is illustrated in detail in FIGS. 3–8 to which specific reference is now made. Handpiece unit 11 includes an integrally formed lightweight metal body member 40 of generally cylindrical configuration. Body member 40 is sealed at its rearward end by end cap 13 and at its forward end by locking ring 16. A slightly radially enlarged flange 42 terminates the rearward end of body member 40 as best illustrated in FIGS. 6 and 6a. The forward portion 41 of body member 40 occupies approximately twenty percent of the length of that member and is cylindrical with a somewhat larger outer-diameter than the remainder of the length of body member 40. Typically, for a body member 40 having a length of 6.57 inches, the outer diameter of forward section 41 would be 1⅜ inches, while the outer diameter of the remainder of the body member 40 would be 1.2 inches. However, forward section 41 is not disposed coaxially with respect to the remainder of body member 40. In this regard, it is helpful to consider body member 40 as having a top side and a bottom side. The top side (which is seen in plan in FIG. 4 and appears as extending along the top of the body member in FIGS. 3 and 6), is considered to be angularly centered on the line which divides switch cluster 17 into two equal transverse halves and extends longitudinally along the outside of member 40. The bottom side of body member 40 is located diametrically opposed to the top side. As best illustrated in FIGS. 3 and 6, the top side of forward section 41 is longitudinally continuous (i.e., forming a straight line) with the top side of the remainder of body member 40. At all other angular positions about the body member, forward section 41 is transversely larger than the rest of the body member 40. The transverse dimensional difference between forward section 41 and the rest of body member 40 increases with angular displacement from the top side of the bottom member to a maximum difference occurring at the bottom side of the member. The transition between forward section 41 and the rest of body member 40 takes the form of a chamfered surface 43 subtending an angle of approximately 45° with the longitudinal dimension of body member 40. The overall effect of the enlarged forward section 41 is a barrelled-out portion of the body member at its forward end.

As best illustrated in FIG. 6, a longitudinally-extending cylindrical bore 44, having a series of sections of different diameter, is defined entirely through body member 40. Bore 44 is concentrically disposed within forward section 41 but is displaced closer to the bottom of the remainder of body member 40. A rearward section 45 of bore 44 serves to house the drive motor for the unit and, in the described embodiment, is typically 4.475 inches long and has a diameter of 0.805 inches. Immediately forward of bore section 45 is a shorter section 46 of smaller diameter in which the motor drive shaft engages the cutting blade. Bore section 46, in the disclosed embodiment, is typically 0.805 inches long with a diameter of 0.565 inches. The next forward bore section 47 serves as an aspirator communication compartment and, in the disclosed embodiment, is typically 0.500 inches long and 0.750 inches in diameter. A short section 48 (i.e., typically 0.060 inches long, 0.565 inches in diameter) separates the aspiration communication chamber 47 from a housing section for an O-ring 49. The O-ring housing section is typically 0.110 inches long and 0.750 inches in diameter. Finally, the forward-most bore section 50 serves to receive the hub of the cutting blade. Bore section 50 is typically 0.620 inches long and 0.565 inches in diameter. The transitions between all bore sections are annular shoulders.

The motor assembly includes a cylindrical motor 51 disposed in bore section 45 and from which a rotatably driven pin 52 projects longitudinally in a forward direction into a hollow cylindrical spacer 55. Spacer 55 remains stationary and has a hollow cylindrical drive tube 56 disposed concentrically therein. Drive tube 56 is welded, tightly fit, or otherwise secured about driven pin 52 in radially spaced relation to spacer 55. Driven pin 52 has a generally rectangular transverse cross-section and is engaged in a bifurcated rearward end 53 of a drive shaft 54 which is also received in and secured to drive tube 56. Thus, when the motor is actuated, driven pin 52 is rotated and rotatably drives the drive tube 56 and drive shaft 54. A stationary bearing housing 57 is disposed immediately forward of spacer 55 to provide a bearing support for the rotatable drive shaft extending therethrough. A plurality of O-rings 58, 59 are disposed about bearing housing 57 and serve as pressure seals in a longitudinal direction in bore section 45. Additional pressure sealing is provided by a gasket 60 disposed adjacent the annular shoulder demarcating the transition between bore sections 45 and 46 and adjacent which the forward-facing end of bearing housing 57 is forcefully urged. In this regard, the housing for motor 51 is provided with a pair of diametrically opposed apertures 61 proximate the rearward end of the motor so that pins (not shown) can be inserted transversely through suitably provided openings in the handpiece body member 40 to lock the motor assembly in place against gasket 60.

The forward end of drive shaft 54 projects into bore section 46 wherein it receives a drive tang 72, projecting from the rearward end of the cutting blade, in rotatably drivable engagement. The cutting blade assembly is illustrated in greater detail in FIGS. 9, 16 and 17 to which specific reference is now made. The cutting blade assembly includes an outer member 70 and an inner member 71. The inner member includes a tube 74 with a distal cutting end 73 which, in the illustrated embodiment, is an arthroplasty burr, although other blade types (such as meniscal open end, meniscal side cutter, end cutter, trimmer, meniscus cutter, synovial resector, and full radius resector) may be employed. Each cutting blade tube 74 is hollow and has an opening 75 proximate the distal end 73 to admit excised tissue aspirated from the surgical site in response to suction applied at the proximal end of the tube. The proximal end 76 of tube 74 is disposed in a molded member having a frusto-conical forward section 78, a hollow intermediate section 77 and a rearward section comprising the drive tang 72. A bore extends transversely through the intermediate section 77 which is recessed to a reduced radial dimension at the bore openings 79. The proximal end 76 of the hollow cutting blade tube 74 communicates with this bore so that aspirated material received in tube 74 can flow out of the cutting blade through bore openings 79. Drive tang 72 is received in a cup-like spring retainer member 80 that is open at both ends.

Spring retainer member 80 has an annular lip projecting radially inward at its forward end and adapted to engage a radially outward projecting lip on the rearward section of the molded member from which drive tang 72 extends. The molded member, including sections 78, 77 and 72, and spring retainer 80 are preferably made of plastic so that the spring retainer can be forced into place on the molded member into a position whereby the two lips prevent mutual disengagement. A helical spring 81 is disposed inside spring retainer 80 to surround the drive tang 72 and serve to bias the rearward end of the spring retainer away from the blade. In this manner, spring 81 urges the two annular lips axially against one another in the absence of any axial force in opposition to the spring. Whereas tube 74 and burr 73 are made of metal (preferably stainless steel), the remainder of the inner member 71 is preferably made of plastic.

Outer member 70 includes a hollow metal (preferably stainless steel) tube 82 having an inside diameter which is larger than the outside diameter of tube 74 in inner member 71. The length of tube 82 is such that the distal end of tube 74, including the cutting blade 73 and opening 75, project through, the open distal end of tube 82 when inner member 71 is inserted into and through inner member 70 in the manner described below. In this regard, the inner and outer members are conventional. Tube 82 extends through a hollow hub preferably made of plastic material and having a short hollow frusto-conical forward end 83 formed integrally with a cylindrical section 84 having an annular rearward-facing surface that is ultrasonically welded or otherwise sealingly disposed against a fixed forward-facing annular surface 85 of a hollow cylindrical section 86. Immediately rearward of hollow section 86 is a hollow cylindrical section 87 of reduced outer diameter. A proximal end section 88 of the hub takes the form of a hollow cylinder with an outer diameter corresponding to that of sections 86 and 84. A central bore 89 extends longitudinally through the integrally formed molded plastic sections 86, 87 and 88 and is generally cylindrical except at its proximal end where it has a frusto-conical contour 90 to receive the frusto-conical section 78 of the inner member 71. Bore 89 is sized to permit tube 74 to extend therethrough, and through a similar aligned bore in sections 83 and 84, into tube 82. The cutting blade, when thusly assembled, has the forward-facing annular shoulder of section 77 of the inner member 71 disposed proximate the rearward-facing proximal end of rearward section 88 of outer member 70. The arrangement permits the inner member 70 to rotate within outer member 70 about the axis of tube 74.

As best illustrated in FIGS. 16 and 17, one or more cylindrical recesses 91 are defined in hub section 86 at the forward-facing surface 85. The number of such recesses 91 provided for any given cutting blade depends upon the optimal rotational speed range for that blade. Specifically, there are three possible speed ranges in the system of the preferred embodiment, although it will be apparent that any number of speed ranges may be designed into the system. For low speed blades, hub section 86 has no recesses defined in surface 85. For medium speed blades, hub section 86 has one recess 91 defined therein at a location radially spaced from the central bore 89 (as illustrated in FIG. 16). For high speed blades, hub 86 has two recesses 91 disposed symmetrically on opposite sides of the central bore 89 (as illustrated in FIGS. 17). Each recess 91 receives a magnet 92 that serves as a coding element for the blade. The material from which the hub is fabricated must be such as to permit the magnetic field of magnets 92 to be sensed in handpiece 11 when the cutting blade is inserted therein (in the manner described below). In order to assure proper orientation of magnet 92 in the handpiece, hub section 86 is formed with a locator stub 93 projecting a short distance radially outward from section 86 at a prescribed annular location on the hub circumference. Specifically, stub 93 is displaced 90° from each of the two possible angular orientations of recesses 91.

Referring again to FIGS. 3–8, locking ring 16 is provided with a central aperture 101 extending longitudinally therethrough and aligned with bore section 50 in body member 40. The diameters of aperture 101 and bore section 50 are slightly greater than the diameter of hub sections 86 and 88 and spring retainer 80. Locator stub 93 in hub sections 86, however, projects radially beyond the boundary of aperture 101 and bore section 50. In order to permit the cutting blade assembly to be accommodated into the handpiece through aperture 101, a radially-extending slot 102 is defined in locking ring 16 at the periphery of aperture 101. A corresponding radially-extending slot 103 is disposed at the periphery of bore section 50 and is sized to permit locator stub 93 to be received therein when the cutting blade assembly is inserted into the handpiece in the manner described below.

As best illustrated in FIG. 10, the forward-facing end surface 104 of body member 40 is provided with two generally cylindrically recesses 105, 106 disposed on diametrically opposite sides of bore section 50 and radially spaced from that bore section. Recesses 105 and 106 are spaced on opposite sides and 90° from slot 103, and each has a generally cylindrical reed switch assembly 107 disposed therein. Reed switch assembly 107, which is illustrated in greater detail in FIG. 11, includes a pair of normally open switch contacts 108, 109 embedded in a glass capsule 12 or potting compound, along with respective lead wires 110, 111 which are insulated and extend from the rearward end of the capsule. The reed switches are oriented to sense the presence of respective magnets 93 in the blade assembly hub so as to register the coded information from the inserted blade. This information, in the form of open/closed conditions of contacts 108, 109, is transmitted to the control circuitry in the console 10 via wires 110, 111. The insulated wires 110, 111 at the rear of the reed switch assembly pass into respective recesses 105, 106 and through respective obliquely oriented wire-conducting channels 113, 114. These channels terminate in a generally rectangular recessed space 115 in the top side of forward section 41, immediately below the switch cluster 17 and its associated printed circuit board 116. The rear wall of recess 115 opens to a channel 117 that runs rearwardly for the remaining length of body member 40. Channel 117 conducts reed switch wires 110, 111 and wires from printed circuit board 116 to the rearward end of body member 40 where the wires form part of cable 12 along with the wires connected to motor 51. The wires in cable 12 conduct signals to and from the circuitry in the control console.

A bore 118 extends from the forward end of surface 104 of body member 40 into recess 115. Bore 118 is used during assembly of the handpiece unit as an access opening for potting compound. Once sufficient potting compound has been delivered into the handpiece, bore 118 is sealed by a set screw 119 and additional compound.

Referring again to FIG. 6, an aspiration path for excised tissue material flowing through hollow tube 74 FIGS. 5 and 9 and out through bore openings 79 in the cutting blade is provided via widened bore section 47. Specifically, when the cutting blade assembly is properly inserted into the handpiece, section 77 of the molded part of the inner blade member 71 is disposed within bore section 44. Openings 79 are clear from the bore walls to permit aspirated material to flow into bore section 47 and through an oblique channel 120 extending both rearwardly and toward the top side of body member 40 until terminating in a suction channel 121. This suction channel extends rearwardly in parallel spaced relation to wire channel 117 until reaching the rearward end of body member 40 where it communicates, via end cap 13, with suction tube 14. As described above, the suction tube 14 communicates with a source of suction pressure (not shown) via a control valve (not shown) to permit selective aspiration from the surgical site. The O-ring 49 disposed in bore section 48 surrounds hub section 86 of the cutting blade assembly to provide a pressure seal forwardly of the aspiration chamber formed by bore section 44. Gasket 60 and O-rings 58, 59 provide pressure seals rearwardly of the aspiration chamber.

Locking ring 16 is a generally cylindrical member having an exposed forward-facing surface 130 and a rearward-facing surface 131 abutting surface 104 of body member 40. The locking ring is made of metal and includes a raised annular lip surrounding surface 131 and extending over a short length of the body member 40. A circular recess 132 in surface 130 is disposed concentrically about aperture 101. Arcuate channels 133, 134 are defined through the locking ring within recess 132. Channels 133 and 134 are equally spaced from slot 102 and are disposed symmetrically about aperture 101. Each channel subtends approximately 90° of arc at a constant radial distance from the center of aperture 101. A disc-shaped spacer 135 is disposed in recess 132 and is provided with a central aperture 140, aligned with aperture 101, and with two screw holes spaced by 180° and aligned with corresponding tapped bores in forward end surface 104 of body member 40. Screws 136, 137 pass through the screw holes and are threadedly engaged in the tapped bores to secure spacer 135 to body member 40. These screws pass through respective channels 134, 133 to permit locking ring 16 to be rotated relative to spacer 135 and body member 40. Such rotation is limited by the lengths of the channels 133, 134 (i.e., 90°). Spacer 135 also has a slot 138 defined therethrough to extend radially from central aperture 140. When slot 138 is rotatably aligned with slot 102 in locking ring 16, and with slot 103 in bore section 50, locator stub 93 on the cutting blade assembly can freely pass into and out of the body member 40.

The rearward-facing side of the locking ring 16, as seen in FIGS. 7 and 8, includes an arcuate ramp surface 141 extending approximately 140° from slot 102 along the outer edge of aperture 101 and the inner edge of arcuate slot 134. Ramp surface 141 serves as a camming surface for inserting the cutting blade into the handpiece. Specifically, in one extreme rotational position of locking ring 16, slot 102 is aligned with slot 138 in spacer 135 and with slot 103 in bore section 50. It is to be noted that slots 138 and 103 are permanently aligned but that slot 102 can be misaligned as a function of the rotation of the locking ring. When all the slots are aligned, the cutting blade assembly may be inserted through the locking ring as far as possible. The open rearward end of the spring retainer member slides over the forward end of the motor drive shaft 54 (as best illustrated in FIG. 6) until the edge of the opening in member 84 abuts the frusto-conical surface of the drive shaft immediately rearward of the forward end of the drive shaft. In this position the locator stub 93 on the cutting blade hub is disposed substantially entirely in slot 103 in bore section 50 with just a small portion of the stub projecting partially into slot 102 of the locking ring. If the locking ring is then rotated 90° to its other extreme position, the camming surface 141 gradually forces stub 93, and with it the cutting blade assembly, rearwardly. This pushes the drive tang 72, in opposition to the bias force of spring 81, further rearward in spring retainer 80 and into more positive engagement with the drive shaft 54. Thus, in the installed position of the blade assembly, spring 81 is axially compressed as camming surface 141 forces locator stub fully into the slot 103 in bore section 50.

In order to remove the cutting blade assembly, the locking ring is rotated 90° in the opposite direction to its initial extreme position, thereby gradually releasing the compression force on spring 81. When slot 102 becomes aligned with slots 138 and 103, spring 81 forces the cutting blade assembly slightly forward so that a portion of stub 93 extends into slot 102. The blade assembly may then be easily removed and replaced by another blade.

The two extreme positions of the locking ring are maintained by means of a detent ball 143 and spring 144 located in a recess in forward-facing surface 104 of body member 40. The detent ball and spring cooperate with two dimples 145, 146 formed at 90° spaced locations in the rearward-facing surface of the locking ring to provide stops at the two extreme rotational positions of the locking ring. Dimples 145 and 146 are configured as spherical segments to match the configuration of ball 143. The locking ring 16 is retained in fixed axial or longitudinal position between the spacer 135 and body member 40 by means of screws 136, 137, but is free to rotate with respect to the spacer and body member by virtue of the 90° channels 133 and 134 that slide about the screws.

An important feature of the present invention is the switch cluster 17 located on the top side of body member 40 in forward section 41. Specifically, and referring to FIG. 6, a printed circuit board 116 is contoured to fit into a shallow recess in forward section 41 of body member 40. This shallow recess surrounds the deeper recess 115 so that lead wires from the printed circuit board can pass into the recess 115 and through wire conducting channel 117 to the cable assembly. The printed circuit board 116 is illustrated in greater detail in FIG. 14 and is transversely arcuate to match a segment of the circumference of forward section 41 of body member 40. Typically, the printed circuit board 116 is made from a rectangular blank or sheet of decarburized steel having a length (i.e., longitudinally of body member 40) of 0.998 inches, a width (i.e., along the circumference of forward section 41) of 1.294 inches and a thickness of 0.013 inches. The sheet is bent to be curved about its longitudinal center line with a radius of curvature of approximately 0.656 inches and so as to subtend an arc of 113° It is to be understood that these dimensions are by way of example only are and not to be construed as limiting on the scope of the invention, except for the considerations set forth below. A layer of porcelain is deposited on each surface of the sheet, and the metal circuit elements are deposited, dr otherwise formed, on the top porcelain surface. A pair of flaps 187, 188 at the center of the sheet are bent downwardly into recess 115 to provide access for lead wires running from the deposited circuitry on the top surface of the board to the handpiece cable via channel 117. The particular materials used in fabricating the printed circuit board 116 are important since the board must withstand autoclave temperatures without becoming brittle and breaking. This becomes a particularly important consideration where, as here, the printed circuit board must be curved at a relatively small radius of curvature. Typically, in order for the printed circuit board to conform to the curvature of the handpiece circumference, the radius of curvature is on the order of 0.6 to 0.7 inches, and usually is in the narrower range of 0.64 to 0.66 inches. Although the decarburized steel sheet with porcelain coatings on both sides is suitable for the printed circuit board of the present invention, I have found that other materials are also suitable. For example, the printed circuit board may be a sheet of aluminum on which a thick film process is employed to form a layer of epoxy with gold silk screening to define the circuit elements. Alternatively, the board may be a thin film TEFLON (polytetrafluoroethylene) weave board with copper laminate used to form the circuit elements. Another alternative is a fiberglass epoxy substrate with copper laminate forming the circuit elements.

Referring to FIGS. 12, 13, and 15, an integral electrically non-conductive silicone rubber sheet 150, having a Durometer on the order of seventy, is disposed atop the printed circuit board 116. A plurality of resilient push button switches 151, 152, 153 and 154 are defined in sheet 150. Each of pushbutton switches 151, 152 and 153 includes a resilient dome-like member 155 tapering from an open end facing the printed circuit board 116 to a closed end 156 remote from the printed circuit board. The closed end 156 encompasses a smaller area and has a smaller periphery than the open end. An electrically conductive member 157 is secured to the underside of the closed end 156. The electrically conductive member of each of pushbuttons 151, 152 and 153 is normally disposed in spaced alignment between a respective pair of contacts on the printed circuit board so that, when the pushbutton is depressed, those contacts are electrically bridged by the conductive member 157. Pushbutton switch 151 has a square-shaped closed end 156 and serves as the forward/reverse control switch. Pushbutton switches 152 and 153 are circular and serve as the decrease speed and increase speed control switches, respectively, for the motor. Pushbutton switches 151, 152 and 153 are disposed in transversely aligned spaced relation along the circumference of the handpiece.

Pushbutton switch 154 is the on/off control switch for the motor and is generally oval-shaped. In this regard pushbutton switch 154 is slightly rearward of the aligned switches 151–153 and has a length along the circumference of the handpiece which corresponds approximately to the total spaced length of the aligned switches 151–153. In this manner the on/off switch 154 is immediately proximate any of the other three switches and can be quickly actuated to turn the motor on or off. Pushbutton switch 154 is also formed as a dome-like member 158 with a closed small end 159 and an open larger end. Three electrically conductive members 160, 161, 162 are secured in transversely spaced relation (i.e., in the same spaced relation as pushbutton switches 151, 152 and 153) to the underside of closed end 159 and are positioned opposite three respective pairs of contacts on the printed circuit board 116. These printed circuit board contacts are connected electrically parallel to one another so that bridging of any one or more of the contact pairs effects the same on/off function. In the preferred embodiment, electrically conductive member 160 is longitudinally aligned with electrically conductive member 157 of switch 151; electrically conductive member 161 is longitudinally aligned with electrically conductive member 157 of switch 152; and electrically conductive member 162 is longitudinally aligned with electrically conductive member 157 of switch 153. The transverse spacing of conductive members 160, 161 and 162 assure that substantially any location along the transverse dimension of switch 154 can be depressed to effect actuation of the on/off function. In this regard, the transverse spacing between successive electrically conductive members 160, 161 and 162 is only slightly greater than the transverse dimension of each of these individual electrically conductive members. For the given Durometer of sheet 150, effective actuation of switch 154 may be achieved from anywhere along the transverse dimension of that switch.

The circuitry on printed circuit board 116 is illustrated in FIG. 14 to which specific reference is now made. All contact pairs for all four switches 151, 152, 153 and 154 include one contact associated with a common lead 170 serving as a circuit ground in the system control circuitry. In this regard, lead 170 surrounds the other leads on three sides and includes six contacts 171, 172, 173, 174, 175 and 176 at spaced locations along its length. A second lead 177 is associated only with on/off switch 154 and includes three contacts 178, 179 and 180 along its length. Contacts 176 and 178 are closely spaced from one another and are positioned under electrically conductive member 162 to be electrically bridged by that member when it is pressed against the printed circuit board 116. In a similar manner contacts 175 and 179 are positioned to be selectively bridged by conductive member 161, and contacts 174 and 180 are positioned to be selectively bridged by electrically conductive member 160.

A third lead 181 has a single contact 182 positioned adjacent but spaced from ground contact 173 so that these two contacts can be selectively bridged by the electrically conductive member 157 of the forward/reverse switch 151. A fourth lead 183 has a single contact 184 positioned adjacent but spaced from ground contact 172 so that these two contacts can be selectively bridged by the electrically conductive member 157 of the decrease speed switch 152. A fifth lead 185 has a single contact 186 positioned adjacent but spaced from ground contact 171 so that these two contacts can be selectively bridged by the electrically conductive member 157 of the increase speed switch 153.

All five leads 170, 177, 181, 183 and 185 extend along one or the other of the centrally located and downwardly bent flaps 187, 188 to connect to appropriate wires in recess 115. As noted above, such wires are conducted through channel 117 to the cable assembly at the rearward end of the handpiece.

A metal cover plate or bezel 190 is disposed over sheet 150 and is apertured to permit pushbuttons 151, 152, 153 and 154 to project therethrough. A plurality of screw holes disposed about the border of plate 190 are aligned with respective holes in sheet 150 and with edge notches in printed circuit board 116 in order to secure these elements together and to body member 40 via respective screws threadedly engaging respective tapped bores in the shallow body member recess in which printed circuit board 116 resides.

All of the components of the handpiece 11 are made of materials that are capable of withstanding the high temperatures to which they are exposed when the handpiece is sterilized by autoclaving or the like. A potting compound or epoxy is used to protect the electrical components from damage during autoclaving.

With brief reference to FIG. 9, the forward section 84 of the hub member for the cutting blade may be colored in a manner to match the border of one of the indicators 26, 27, 28 so as to provide a color-coded indication on the cutting blade of the speed range corresponding to the correspondingly color coded indicator border.

The body member 40 is made of lightweight material and is balanced to facilitate small joint arthroscopy. Longitudinally-extending fluting along the length of the body member facilitates handling. The body member houses a powerful brushless motor providing the necessary torque and speed for all types of powered arthroscopic procedures. The location of switch cluster 17 on the handpiece greatly facilitates operation by the surgeon. Automatic speed range is provided without the need for heavy adapters which must be sterilized after each surgical procedure. Although the motor may be completely controlled from the handpiece, a footswitch is provided to permit control over forward and reverse rotation while allowing the surgeon to select the proper speed from the handpiece. The entire handpiece and cord may be immersed and soaked in a sterilized solution without corroding. In addition, the unit may be flashed, steamed autoclaved or gas sterilized. The use of disposable, single-use cutting blades assures factory-fresh sharpness with every surgical procedure and eliminates the expense and time delay involved in sharpening and re-sharpening blades.

It is to be understood that the various specific dimensions presented by way of example herein are intended to be only exemplary unless otherwise stated.

From the foregoing description it will be appreciated that the invention makes available a novel drive system for an arthroscopic surgical instrument wherein the drive motor may be entirely controlled from the handpiece and wherein automatic speed range control is effected by directly coding the cutting blade assembly and thereby eliminating the need for an intermediate adapter. The unique arcuate printed circuit board, serving as part of the handpiece control switch cluster, permits that cluster to be contoured to fit generally within the contour of the handpiece so that the handpiece itself may be more easily manipulated and so that the individual switches in the switch cluster may be quickly and accurately accessed.

Having described a preferred embodiment of a new and improved electrosurgical instrument constructed in accordance with the present invention, it is believed that other modifications, variations and changes will be suggested to those skilled in the art in view of the techniques set forth herein. It is therefore to be understood that all such variations, modifications and changes are believed to fall within the scope of the present invention as defined in the appended claims.

```
FILE: TORQ4:GH          HEWLETT-PACKARD: INTRA-ARC DRIVE PROGRAM
            Fr    23 Jan 1987, 18:27      P    1
LOCATION OBJECT CODE LINE    SOURCE LINE

1         "Z80"    LIST
                         3    ; CONCEPT, INC. - FRED REXROTH MAR 14,1986
                         4    * DWG. NO. 149-132 REV F
                         5    *
         <0006>          6  REVLEV  EQU     6         ;PROG REV LEV
         <0000>          7  SEG     DEFL    00H
         <0090>          8  SEG2    DEFL    90H
         <0010>          9  BAR1    DEFL    10H
         <0020>         10  BAR2    DEFL    20H
         <0080>         11  BAR3    DEFL    80H
         <0030>         12  DAC     DEFL    30H
         <0040>         13  FSW     DEFL    40H
         <0050>         14  HSW     DEFL    50H
         <0060>         15  LITE    DEFL    60H
                        16  ***
                        17          EXT     FLOT
                        18          EXT     FIXX
                        19          EXT     FMPY
                        20          ORG     0000H
0000 DD2143FF           21          LD      IX,43FFH   ;SP ADR
0004 DDF9               22          LD      SP,IX
0006 F3                 23          DI                 ;NO INTERRUPT
0007 210001             24          LD      HL,0001H
000A 224017             25          LD      [CTR5],HL
000D 3E08               26          LD      A,8
000F 324016             27          LD      [CTR4],A
0012 3E00               28          LD      A,00H
0014 324000             29          LD      [INBUF],A
0017 32400F             30          LD      [FLAGS],A
001A D330               31          OUT     [DAC],A
001C CD0778             32          CALL    CHECK      ;LIGHTS TEST
001F C300AC             33          JP      MOTOK
0022 DB40               34  IDLE    IN      A,[FSW]
0024 CB47               35          BIT     0,A        ;FSW IN ?
0026 200F               36          JR      NZ,NOFSW   ;JP IF NO
0028 3A4000             37          LD      A,[INBUF]
002B CBF7               38          SET     6,A
002D 324000             39          LD      [INBUF],A
0030 3A4003             40          LD      A,[OUTBUF]
0033 CBE7               41          SET     4,A        ;FSW LITE ON
0035 180D               42          JR      JP1
0037 3A4000             43  NOFSW   LD      A,[INBUF]
003A CBB7               44          RES     6,A
003C 324000             45          LD      [INBUF],A
003F 3A4003             46          LD      A,[OUTBUF]
0042 CBA7               47          RES     4,A        ;FSW LITE OFF
0044 324003             48  JP1     LD      [OUTBUF],A
0047 D360               49          OUT     [LITE],A
0049 AF                 50          XOR     A          ;ZERO A REG
004A 32401C             51          LD      [OLDINB],A
004D D330               52          OUT     [DAC],A    ;MIN RPM
004F 3A4003             53          LD      A,[OUTBUF]
0052 CB97               54          RES     2,A        ;ACTIVATE STOP
0054 324003             55          LD      [OUTBUF],A
0057 D360               56          OUT     [LITE],A   ;STOP
0059 328000             57  OPER    LD      [8000H],A
005C 326000             58          LD      [6000H],A
```

```
FILE: TORQ4:GH           HEWLETT-PACKARD: INTRA-ARC DRIVE PROGRAM
         Fri, 23 J   1987, 18:27      PAGE   2
LOCATION OBJECT CODE LINE      SOURCE LINE

005F DB40          59           IN     A,[FSW]
  0061 CB6F          60           BIT    5,A         ;MOT CB TRIP
  0063 2847          61           JR     Z,MOTOK     ;NO, JP
  0065 0E00          62           LD     C,SEG
  0067 3A400F        63           LD     A,[FLAGS]
  006A CB67          64           BIT    4,A         ;DSPLY TO ZERO ?
  006C 2812          65           JR     Z,SETZ      ;YES JP
  006E 3E00          66           LD     A,00H
  0070 ED79          67           OUT    [C],A
  0072 3E10          68           LD     A,10H
  0074 ED79          69           OUT    [C],A
  0076 3E20          70           LD     A,20H
  0078 ED79          71           OUT    [C],A
  007A 3E30          72           LD     A,30H
  007C ED79          73           OUT    [C],A
  007E 1810          74           JR     CKCTR
  0080 3E0F          75   SETZ    LD     A,0FH
  0082 ED79          76           OUT    [C],A
  0084 3E1F          77           LD     A,1FH
  0086 ED79          78           OUT    [C],A
  0088 3E2F          79           LD     A,2FH
  008A ED79          80           OUT    [C],A
  008C 3E3F          81           LD     A,3FH
  008E ED79          82           OUT    [C],A
  0090 2A4017        83   CKCTR   LD     HL,[CTR5]
  0093 2B            84           DEC    HL
  0094 224017        85           LD     [CTR5],HL
  0097 7C            86           LD     A,H
  0098 B5            87           OR     L
  0099 2087          88           JR     NZ,IDLE
  009B 3A400F        89   RLOAD   LD     A,[FLAGS]
  009E EE10          90           XOR    10H
  00A0 32400F        91           LD     [FLAGS],A
  00A3 210FFF        92           LD     HL,0FFFH
  00A6 224017        93           LD     [CTR5],HL
  00A9 C30022        94           JP     IDLE
  00AC CD00D0        95   MOTOK   CALL   RANGE       ;SET SPEED RANGE
  00AF CD016D        96           CALL   SPDX        ;SPEED CHANGE
  00B2 CD031C        97           CALL   MODE        ;MOTOR DIR
  00B5 CD04CB        98           CALL   BNBCD       ;DECIMAL SPEED
  00B8 CD0523        99           CALL   DISP        ;DIGITS/LITES
  00BB FD210300      100          LD     IY,0300H
  00BF CD0652        101          CALL   WAIT
  00C2 3A4000        102          LD     A,[INBUF]
  00C5 CB67          103          BIT    4,A
  00C7 CA0022        104          JP     Z,IDLE      ;? RUN MOTOR
  00CA CD0665        105          CALL   RUN
  00CD C30059        106          JP     OPER
                     107  *
                     108  *** SUBROUTINE TO SET SPEED RANGE ***
  00D0 214000        109  RANGE   LD     HL,INBUF
  00D3 7E            110          LD     A,[HL]
  00D4 CB7F          111          BIT    7,A         ;FULL SPD RNG ?
  00D6 C0            112          RET    NZ          ;RET IF YES
  00D7 DD214001      113          LD     IX,SPLB
  00DB DB50          114          IN     A,[HSW]
  00DD E603          115          AND    03H         ;MASK
```

FILE: TORQ4:GH          LETT-PACKARD: INTRA-ARC  VE PROGRAM
        Fri, 23 J    1987, 18:28    PAGE    3

LOCATION OBJECT CODE LINE    SOURCE LINE

```
00DF 47              116              LD      B,A
00E0 7E              117              LD      A,[HL]
00E1 E603            118              AND     03H         ;CP OLD CODE
00E3 B8              119              CP      B
00E4 C8              120              RET     Z
00E5 78              121              LD      A,B
00E6 FE00            122              CP      00H         ;?SHAVER
00E8 2013            123              JR      NZ,RESCT
00EA 110891          124              LD      DE,LORNG    ;SET HI LO LIM
00ED CD015C          125              CALL    DIGITS
00F0 1100EB          126    FALT      LD      DE,235D
00F3 DD7300          127              LD      [IX+0],E
00F6 DD7201          128              LD      [IX+1],D
00F9 3E0C            129              LD      A,0CH
00FB 77              130              LD      [HL],A
00FC C9              131              RET
00FD FE02            132    RESCT     CP      02H         ;?RESECTOR
00FF 2016            133              JR      NZ,BURR
0101 110899          134              LD      DE,MIDRNG   ;SET HI LO LIM
0104 CD015C          135              CALL    DIGITS
0107 1102BC          136              LD      DE,0700D
010A DD7300          137              LD      [IX+0],E
010D DD7201          138              LD      [IX+1],D
0110 3E0E            139              LD      A,0EH
0112 77              140              LD      [HL],A
0113 CD0131          141              CALL    FWDBIT
0116 C9              142              RET
0117 FE01            143    BURR      CP      01H         ;?BURR
0119 20D5            144              JR      NZ,FALT
011B 1108A1          145              LD      DE,HIRNG    ;SET HI LO LIM
011E CD015C          146              CALL    DIGITS
0121 1107D0          147              LD      DE,2000D
0124 DD7300          148              LD      [IX+0],E
0127 DD7201          149              LD      [IX+1],D
012A 3E0D            150              LD      A,0DH
012C 77              151              LD      [HL],A
012D CD0131          152              CALL    FWDBIT
0130 C9              153              RET
                     154    *
0131 3A4000          155    FWDBIT    LD      A,[INBUF]
0134 CBD7            156              SET     2,A         ;SET MOT FWD
0136 324000          157              LD      [INBUF],A
0139 210150          158              LD      HL,OUTF
013C 180B            159              JR      CKMOT
013E 3A4000          160    REVBIT    LD      A,[INBUF]
0141 CB97            161              RES     2,A         ;SET MOT REV
0143 324000          162              LD      [INBUF],A
0146 210154          163              LD      HL,OUTR
0149 3A4003          164    CKMOT     LD      A,[OUTBUF]
014C CB57            165              BIT     2,A         ,MOT ON ?
014E C0              166              RET     NZ          ;RET IF YES
014F E9              167              JP      [HL]
0150 CBCF            168    OUTF      SET     1,A
0152 1802            169              JR      OLITE
0154 CB8F            170    OUTR      RES     1,A
0156 324003          171    OLITE     LD      [OUTBUF],A
0159 D360            172              OUT     [LITE],A
```

```
FILE: TORQ4:GH           ‎LETT-PACKARD: INTRA-ARC ‎  VE PROGRAM
          Fri, 23 J   1987, 18:28     PAGE   4
LOCATION OBJECT CODE LINE     SOURCE LINE

015B C9             173          RET
                       174 *
                       175 *** SUBROUTINE TO DRIVE 7 SEGMENT DISPLAYS
   015C 0E90           176 DIGITS   LD    C,SEG2
   015E 0600           177          LD    B,00H
   0160 210008         178          LD    HL,08H
   0163 CD0586         179 NXTDIG   CALL  DIGIT
   0166 2D             180          DEC   L
   0167 20FA           181          JR    NZ,NXTDIG
   0169 214000         182          LD    HL,INBUF
   016C C9             183          RET
                       184 *** SUBROUTINE TO CHANGE SPEED ***
   016D DD214001       185 SPDX     LD    IX,SPLB
   0171 DB50           186          IN    A,[HSW]
   0173 47             187          LD    B,A         ;SAVE
   0174 CB6F           188          BIT   5,A         ;?SPEED UP
   0176 CA0265         189          JP    Z,SPDN      ;NO,JP
   0179 DD6E00         190          LD    L,[IX+0]
   017C DD6601         191          LD    H,[IX+1]
   017F 3A4000         192          LD    A,[INBUF]   ;TEST RANGE
   0182 E683           193          AND   83H
   0184 FE00           194          CP    00H         ;LO RANGE ?
   0186 205B           195          JR    NZ,MIDR     ;NO, JUMP
   0188 110190         196          LD    DE,0400D
   018B ED52           197          SBC   HL,DE       ;HI LIM ?
   018D 2038           198          JR    NZ,SPDUP    ;NO,JP
   018F CD0310         199          CALL  AUDOFF
   0192 3A4000         200          LD    A,[INBUF]
   0195 CB7F           201          BIT   7,A         ;FULL SPD RNG ACTV ?
   0197 C0             202          RET   NZ          ;YES,JP
   0198 FD21FFFF       203          LD    IY,0FFFFH
   019C CD0652         204          CALL  WAIT
   019F CD0652         205          CALL  WAIT
   01A2 CD0652         206          CALL  WAIT
   01A5 DB50           207          IN    A,[HSW]
   01A7 CB6F           208          BIT   5,A         ;RPM UP SW ACTV ?
   01A9 C8             209          RET   Z           ;NO,RET
   01AA 214000         210          LD    HL,INBUF
   01AD DD214001       211          LD    IX,SPLB
   01B1 1108A9         212          LD    DE,FULRNG
   01B4 CD015C         213          CALL  DIGITS
   01B7 1104E2         214          LD    DE,1250D
   01BA DD7300         215          LD    [IX+0],E
   01BD DD7201         216          LD    [IX+1],D
   01C0 3E8C           217          LD    A,08CH
   01C2 77             218          LD    [HL],A
   01C3 CD0131         219          CALL  FWDBIT      ;SET FWD DIR
   01C6 C9             220          RET
   01C7 DD6E00         221 SPDUP    LD    L,[IX+0]
   01CA DD6601         222          LD    H,[IX+1]
   01CD 23             223          INC   HL
   01CE DD7500         224          LD    [IX+0],L
   01D1 DD7401         225          LD    [IX+1],H
   01D4 3A4000         226          LD    A,[INBUF]
   01D7 CBAF           227          RES   5,A         ;CANCEL JOG
   01D9 324000         228          LD    [INBUF],A
   01DC CD0305         229          CALL  AUDON
```

FILE: TORQ4:GH    ' 'LETT-PACKARD: INTRA-ARC F VE PROGRAM
         Fri, 23 J   1987, 18:28    PAGE   5
LOCATION OBJECT CODE LINE    SOURCE LINE

```
01DF CD02F0       230         CALL    SPEED
01E2 C9           231         RET
01E3 FE02         232 MIDR    CP      02H
01E5 201C         233         JR      NZ,HIR
01E7 110384       234         LD      DE,0900D      ;HI LIMIT
01EA ED52         235         SBC     HL,DE         ;MAX RPM ?
01EC F20310       236         JP      P,AUDOFF
01EF DD6E00       237         LD      L,[IX+0]
01F2 DD6601       238         LD      H,[IX+1]
01F5 23           239         INC     HL
01F6 DD7500       240         LD      [IX+0],L
01F9 DD7401       241         LD      [IX+1],H
01FC CD0305       242         CALL    AUDON
01FF CD02F0       243         CALL    SPEED         ;DELAY
0202 C9           244         RET
0203 1109C4       245 HIR     LD      DE,2500D
0206 37           246         SCF
0207 3F           247         CCF
0208 ED52         248         SBC     HL,DE
020A 203D         249         JR      NZ,RPMUP
020C CD0310       250         CALL    AUDOFF
020F 3A4000       251         LD      A,[INBUF]
0212 CB7F         252         BIT     7,A           ;FULL SPD RNG ?
0214 C8           253         RET     Z             ;RET IF NO
0215 DB50         254         IN      A,[HSW]
0217 CB6F         255         BIT     5,A           ;RPM UP ACTV ?
0219 C8           256         RET     Z             ;RET,IF NO
021A FD21FFFF     257         LD      IY,0FFFFH
021E CD0652       258         CALL    WAIT
0221 CD0652       259         CALL    WAIT
0224 CD0652       260         CALL    WAIT
0227 DB50         261         IN      A,[HSW]
0229 CB6F         262         BIT     5,A           ;RPM UP ACTV ?
022B C8           263         RET     Z             ;RET IF NO
022C 214000       264         LD      HL,INBUF
022F DD214001     265         LD      IX,SPLB
0233 110891       266         LD      DE,LORNG
0236 CD015C       267         CALL    DIGITS
0239 1100EB       268         LD      DE,235D
023C DD7300       269         LD      [IX+0],E
023F DD7201       270         LD      [IX+1],D
0242 3E0C         271         LD      A,0CH
0244 77           272         LD      [HL],A
0245 CD0131       273         CALL    FWDBIT
0248 C9           274         RET
0249 DD6E00       275 RPMUP   LD      L,[IX+0]
024C DD6601       276         LD      H,[IX+1]
024F 23           277         INC     HL
0250 DD7500       278         LD      [IX+0],L
0253 DD7401       279         LD      [IX+1],H
0256 3A4000       280         LD      A,[INBUF]     ;CANCEL JOG
0259 CBAF         281         RES     5,A
025B 324000       282         LD      [INBUF],A
025E CD0305       283         CALL    AUDON
0261 CD02F0       284         CALL    SPEED
0264 C9           285         RET
0265 CB67         286 SPDN    BIT     4,A           ;SP DOWN?
```

```
FILE: TORQ4:GH          HEWLETT-PACKARD: INTRA-ARC DRIVE PROGRAM
            Fri, 23 J  1987, 18:28     PAGE   6

LOCATION OBJECT CODE LINE      SOURCE LINE

0267 CA0310      287         JP      Z,AUDOFF        ;NO JP
  026A DD5E00      288         LD      E,[IX+0]
  026D DD5601      289         LD      D,[IX+1]
  0270 3A4000      290         LD      A,[INBUF]
  0273 E683        291         AND     83H
  0275 FE01        292         CP      01H             ;HI RNG ?
  0277 2018        293         JR      NZ,MRDN         ;NO,JP
  0279 2105DC      294         LD      HL,1500D
  027C 37          295         SCF
  027D 3F          296         CCF
  027E ED52        297         SBC     HL,DE
  0280 CA0310      298         JP      Z,AUDOFF
  0283 1B          299         DEC     DE
  0284 DD7300      300         LD      [IX+0],E
  0287 DD7201      301         LD      [IX+1],D
  028A CD0305      302         CALL    AUDON
  028D CD02F0      303         CALL    SPEED
  0290 C9          304         RET
  0291 FE02        305 MRDN    CP      02H             ;MED RNG ?
  0293 2018        306         JR      NZ,LRDN         ;NO,JP
  0295 2101F4      307         LD      HL,0500D        ;LO LIMIT
  0298 37          308         SCF
  0299 3F          309         CCF
  029A ED52        310         SBC     HL,DE           ;SPD = LO SPD LIMIT ?
  029C CA0310      311         JP      Z,AUDOFF        ;JP IF YES
  029F 1B          312         DEC     DE
  02A0 DD7300      313         LD      [IX+0],E
  02A3 DD7201      314         LD      [IX+1],D
  02A6 CD0305      315         CALL    AUDON
  02A9 CD02F0      316         CALL    SPEED
  02AC C9          317         RET
  02AD 3A4000      318 LRDN    LD      A,[INBUF]
  02B0 CB6F        319         BIT     5,A             ;JOG ACTV ?
  02B2 C0          320         RET     NZ              ;YES JP
  02B3 21004B      321         LD      HL,075D         ;LO LIMIT
  02B6 37          322         SCF
  02B7 3F          323         CCF
  02B8 ED52        324         SBC     HL,DE           ;DE HAS OLD SPEED
  02BA CA02CB      325         JP      Z,ASP
  02BD 1B          326         DEC     DE
  02BE DD7300      327         LD      [IX+0],E
  02C1 DD7201      328         LD      [IX+1],D
  02C4 CD0305      329         CALL    AUDON
  02C7 CD02F0      330         CALL    SPEED
  02CA C9          331         RET
  02CB CD0310      332 ASP     CALL    AUDOFF
  02CE FD21FF00    333         LD      IY,0FF00H
  02D2 CD0652      334         CALL    WAIT
  02D5 DB50        335         IN      A,[HSW]
  02D7 CB67        336         BIT     4,A             ;? SPEED DN
  02D9 C8          337         RET     Z               ;NO JP
  02DA 3A4000      338         LD      A,[INBUF]
  02DD CBEF        339         SET     5,A             ;JOG
  02DF 324000      340         LD      [INBUF],A
  02E2 3A400E      341         LD      A,[GRAPH+2]
  02E5 CBEF        342         SET     5,A             ;TOUCH LITE ON
  02E7 32400E      343         LD      [GRAPH+2],A
```

FILE: TORQ4:GH     ‎'LETT-PACKARD: INTRA-ARC ‎ ‎VE PROGRAM
          Fri, 23 J   1987, 18:28    PAGE   7

LOCATION OBJECT CODE LINE    SOURCE LINE

```
02EA D380         344            OUT     [BAR3],A
02EC CD0131       345            CALL    FWDBIT
02EF C9           346            RET
                  347  *
02F0 FD212FFF     348  SPEED     LD      IY,02FFFH
02F4 3A4016       349            LD      A,[CTR4]
02F7 FE00         350            CP      00H
02F9 F202FD       351            JP      P,SLO
02FC C9           352            RET                     ;FAST SPD EXIT
02FD 3D           353  SLO       DEC     A
02FE 324016       354            LD      [CTR4],A
0301 CD0652       355            CALL    WAIT            ;SLOW SPD EXIT
0304 C9           356            RET
                  357  *
0305 3A4003       358  AUDON     LD      A,[OUTBUF]
0308 CB9F         359            RES     3,A
030A 324003       360  AUDIO     LD      [OUTBUF],A
030D D360         361            OUT     [LITE],A
030F C9           362            RET
                  363  *
0310 3E08         364  AUDOFF    LD      A,08D
0312 324016       365            LD      [CTR4],A
0315 3A4003       366            LD      A,[OUTBUF]
0318 CBDF         367            SET     3,A
031A 18EE         368            JR      AUDIO
                  369  *
                  370  *** SUBROUTINE TO SET MOTOR DIRECTION ***
031C DB50         371  MODE      IN      A,[HSW]
031E 5F           372            LD      E,A
031F CB47         373            BIT     0,A             ;HI SPD RNG ?
0321 203F         374            JR      NZ,FRR          ;YES,JP
0323 DB40         375            IN      A,[FSW]
0325 CB5F         376            BIT     3,A             ;OSC ?
0327 2039         377            JR      NZ,FRR          ;NO,JP
0329 2A4001       378            LD      HL,[SPLB]
032C 010385       379            LD      BC,901D
032F 37           380            SCF
0330 3F           381            CCF
0331 ED42         382            SBC     HL,BC           ;SPD > 900 ?
0333 F20362       383            JP      P,FRR           ;YES,JP
0336 3A4000       384  SETOSC    LD      A,[INBUF]
0339 CB9F         385            RES     3,A             ;SET OSC MODE
033B 324000       386            LD      [INBUF],A
033E 3A400E       387            LD      A,[GRAPH+2]
0341 CBA7         388            RES     4,A
0343 32400E       389            LD      [GRAPH+2],A
0346 D380         390            OUT     [BAR3],A
0348 187E         391            JR      JOG
034A FE01         392  FDRV      CP      01H             ;HI RNG
034C 2014         393            JR      NZ,FRR          ;NO,JP
034E 3A4000       394            LD      A,[INBUF]
0351 CBDF         395            SET     3,A             ;CONT
0353 324000       396            LD      [INBUF],A
0356 3A400E       397            LD      A,[GRAPH+2]
0359 CBE7         398            SET     4,A             ;SET NORM MODE
035B 32400E       399            LD      [GRAPH+2],A
035E D380         400            OUT     [BAR3],A
```

```
FILE: TORQ4:GH          HEWLETT-PACKARD: INTRA-ARC DRIVE PROGRAM
           Fri, 23 _ 1987, 18:28    PAGE   8
LOCATION OBJECT CODE LINE    SOURCE LINE 0360 1812           401          JR     FRCHK
0362 3A4000         402 FRR     LD     A,[INBUF]
0365 CBDF           403         SET    3,A              ;SET CONT MODE
0367 324000         404         LD     [INBUF],A
036A 3A400E         405         LD     A,[GRAPH+2]
036D CBE7           406         SET    4,A              ;SET NORM MODE
036F 32400E         407         LD     [GRAPH+2],A
0372 D380           408         OUT    [BAR3],A
0374 3A4000         409 FRCHK   LD     A,[INBUF]
0377 CB6F           410         BIT    5,A              ;JOG ACTV ?
0379 204D           411         JR     NZ,JOG           ;YES,JP
037B DB40           412         IN     A,[FSW]
037D CB47           413         BIT    0,A              ;FSW IN ?
037F 2835           414         JR     Z,FIN            ;YES,JP
0381 3A4000         415         LD     A,[INBUF]
0384 CBB7           416         RES    6,A              ;RES FSW FLG
0386 324000         417         LD     [INBUF],A
0389 3A400F         418         LD     A,[FLAGS]
038C CB4F           419         BIT    1,A              ;F/R FLG ACTV ?
038E C20474         420         JP     NZ,SW2ACT        ;YES JP
0391 CB53           421         BIT    2,E              ;F/R SW ACTV ?
0393 2833           422         JR     Z,JOG            ;NO,JP
0395 CBCF           423         SET    1,A              ;SET F/R DEB FLG
0397 32400F         424         LD     [FLAGS],A        ;SAVE FLAGS
039A 21001F         425         LD     HL,01FH          ;SET DEB COUNTER
039D 224012         426         LD     [CTR2],HL
03A0 3A4000         427         LD     A,[INBUF]
03A3 EE04           428         XOR    04H              ;TOGGLE BIT 2
03A5 324000         429         LD     [INBUF],A
03A8 CB57           430         BIT    2,A              ;FWD/REV ?
03AA 2805           431         JR     Z,REV            ;JP IF REV
03AC CD0131         432         CALL   FWDBIT           ;SET FWD
03AF 1817           433         JR     JOG
03B1 CD013E         434 REV     CALL   REVBIT           ;SET REV
03B4 1812           435         JR     JOG
03B6 3A4000         436 FIN     LD     A,[INBUF]
03B9 CBF7           437         SET    6,A              ;FSW FLG
03BB 324000         438         LD     [INBUF],A
03BE 3A400E         439         LD     A,[GRAPH+2]
03C1 CBEF           440         SET    5,A              ;TOUCH MODE
03C3 32400E         441         LD     [GRAPH+2],A
03C6 D380           442         OUT    [BAR3],A
03C8 3A4000         443 JOG     LD     A,[INBUF]
03CB CB6F           444         BIT    5,A              ;? JOG MODE
03CD 2813           445         JR     Z,NOJOG          ;JP IF NO
03CF AF             446         XOR    A
03D0 32400F         447         LD     [FLAGS],A
03D3 CD0131         448         CALL   FWDBIT
03D6 3A400E         449         LD     A,[GRAPH+2]      ;SET CONT LITE
03D9 CBE7           450         SET    4,A
03DB 32400E         451         LD     [GRAPH+2],A
03DE D380           452         OUT    [BAR3],A
03E0 1810           453         JR     JOGIT
03E2 DB40           454 NOJOG   IN     A,[FSW]
03E4 CB67           455         BIT    4,A              ;TOUCH OR CONT ?
03E6 202C           456         JR     NZ,AONF          ;JP IF CONT
03E8 3A400E         457         LD     A,[GRAPH+2]
```

FILE: TORQ4:GH    'LETT-PACKARD: INTRA-ARC  VE PROGRAM
          Fri, 23 J  1987, 18:28    PAGE   9

LOCATION OBJECT CODE LINE     SOURCE LINE

```
03EB CBEF         458          SET   5,A
03ED 32400E       459          LD    [GRAPH+2],A
03F0 D380         460          OUT   [BAR3],A
03F2 3A4000       461 JOGIT    LD    A,[INBUF]
03F5 CB77         462          BIT   6,A           ;FSW PLUGED IN?
03F7 200D         463          JR    NZ,CKFSW      ;JP IF YES
03F9 CB5B         464          BIT   3,E           ;HSW ON/OFF ACTV ?
03FB 2809         465          JR    Z,CKFSW       ;NO,JP
03FD 3A4000       466          LD    A,[INBUF]
0400 CBE7         467          SET   4,A           ;RUN MOT
0402 324000       468          LD    [INBUF],A
0405 C9           469          RET
0406 3A4000       470 CKFSW    LD    A,[INBUF]
0409 CB77         471          BIT   6,A           ;FSW IN ?
040B C2049C       472          JP    NZ,FONF       ;YES,JP
040E CBA7         473          RES   4,A           ;STOP MOT
0410 324000       474          LD    [INBUF],A
0413 C9           475          RET
0414 21400F       476 AONF     LD    HL,FLAGS
0417 3A400E       477          LD    A,[GRAPH+2]
041A CBAF         478          RES   5,A
041C 32400E       479          LD    [GRAPH+2],A
041F D380         480          OUT   [BAR3],A
0421 CB46         481          BIT   0,[HL]        ;ON/OFF FLAG ACTIVE ?
0423 202B         482          JR    NZ,SW1ACT     ;YES,JP
0425 3A4000       483          LD    A,[INBUF]
0428 CB77         484          BIT   6,A           ;FSW ACTV ?
042A 20DA         485          JR    NZ,CKFSW      ;YES,JP
042C CB5B         486          BIT   3,E           ;? ON/OFF ACTIVATED
042E 2005         487          JR    NZ,SWON       ;YES,JP
0430 CB5E         488          BIT   3,[HL]        ;MOT ON IN CONT MODE ?
0432 28D2         489          JR    Z,CKFSW       ;NO,JP
0434 C9           490          RET
0435 CBC6         491 SWON     SET   0,[HL]        ;SET ON/OFF DEB ACT
0437 01001F       492          LD    BC,01FH       ;INIT DEB COUNTER
043A ED434010     493          LD    [CTR1],BC
043E 3A4000       494          LD    A,[INBUF]
0441 EE10         495          XOR   10H           ;TOGGLE BIT 4
0443 324000       496          LD    [INBUF],A
0446 CB67         497          BIT   4,A           ;MOT ON ?
0448 2003         498          JR    NZ,FLG3       ;YES,JP
044A CB9E         499          RES   3,[HL]
044C C9           500          RET
044D CBDE         501 FLG3     SET   3,[HL]
044F C9           502          RET
                  503 *
0450 ED5B4010     504 SW1ACT   LD    DE,[CTR1]     ;GET COUNT
0454 1B           505          DEC   DE
0455 7A           506          LD    A,D
0456 B3           507          OR    E             ;COUNT ZERO ?
0457 2016         508          JR    NZ,STDAT1     ;JP IF NO
0459 DB50         509          IN    A,[HSW]
045B CB5F         510          BIT   3,A           ;ON/OFF SW ACTIVE ?
045D 2807         511          JR    Z,RESET1      ;NO,JP
045F 21001F       512          LD    HL,01FH       ;HERE IF ACTIVE
0462 224010       513          LD    [CTR1],HL     ;RESET COUNT LOOP
0465 C9           514          RET
```

```
FILE: TORQ4:GH         HEWLETT-PACKARD: INTRA-ARC DRIVE PROGRAM
         Fri, 23 J   1987, 18:28      PAGE 10

LOCATION OBJECT CODE LINE      SOURCE LINE

515 *
0466 3A400F          516 RESET1  LD      A,[FLAGS]
0469 CB87            517         RES     0,A
046B 32400F          518         LD      [FLAGS],A
046E C9              519         RET
                     520 *
046F ED534010        521 STDAT1  LD      [CTR1],DE       ;RESTORE DATA
0473 C9              522         RET
                     523 *
0474 2A4012          524 SW2ACT  LD      HL,[CTR2]       ;GET COUNT
0477 2B              525         DEC     HL
0478 7C              526         LD      A,H
0479 B5              527         OR      L               ;COUNT ZERO ?
047A 201A            528         JR      NZ,STDAT2       ;JP IF NO
047C DB50            529         IN      A,[HSW]
047E CB57            530         BIT     2,A             ;F/R SW ACTIVE ?
0480 2809            531         JR      Z,RESET2        ;NO,JP
0482 21001F          532         LD      HL,01FH
0485 224012          533         LD      [CTR2],HL       ;RESET DEB COUNTER
0488 C303C8          534         JP      JOG
                     535 *
048B 3A400F          536 RESET2  LD      A,[FLAGS]
048E CB8F            537         RES     1,A
0490 32400F          538         LD      [FLAGS],A
0493 C303C8          539         JP      JOG
                     540 *
0496 224012          541 STDAT2  LD      [CTR2],HL       ;RESTORE
0499 C303C8          542         JP      JOG
                     543 *
049C DB40            544 FONF    IN      A,[FSW]
049E CB4F            545         BIT     1,A             ;FSW FWD ?
04A0 200B            546         JR      NZ,FSREV        ;JP IF NO
04A2 3A4000          547         LD      A,[INBUF]
04A5 CB5F            548         BIT     3,A             ;OSC MODE ?
04A7 2811            549         JR      Z,RUNMOT        ;JP IF YES
04A9 CBD7            550         SET     2,A             ;SET FWD DIR
04AB 180D            551         JR      RUNMOT
04AD CB57            552 FSREV   BIT     2,A             ;FSW REV ?
04AF 200F            553         JR      NZ,FOF          ;JP IF NO
04B1 3A4000          554         LD      A,[INBUF]
04B4 CB5F            555         BIT     3,A             ;OSC MODE ?
04B6 2802            556         JR      Z,RUNMOT        ;JP IF YES
04B8 CB97            557         RES     2,A             ;SET REV DIR
04BA CBE7            558 RUNMOT  SET     4,A             ;RUN MOT
04BC CBF7            559         SET     6,A             ;FSW ON FLG
04BE 1807            560         JR      LDINB
04C0 3A4000          561 FOF     LD      A,[INBUF]
04C3 CBA7            562         RES     4,A             ;STOP MOT
04C5 CBB7            563         RES     6,A             ;FSW FLG OFF
04C7 324000          564 LDINB   LD      [INBUF],A
04CA C9              565         RET
                     566 *
                     567 *** SUBROUTINE TO CONVERT SPEED TO DECIMAL ***
04CB DD214004        568 BNBCD   LD      IX,DISBUF
04CF FD214001        569         LD      IY,SPLB
04D3 AF              570         XOR     A               ;ZERO A REG
04D4 328000          571         LD      [8000H],A
```

```
FILE: TORQ4:GH           ~WLETT-PACKARD: INTRA-ARC ~ 'VE PROGRAM
          Fri, 23 ~ 1987, 18:28    PAGE 11
LOCATION OBJECT CODE  LINE     SOURCE LINE

04D7  326000          572          LD     [6000H],A
04DA  324060          573          LD     [4060H],A
04DD  FD6E00          574          LD     L,[IY+0]     ;BIN IN HL
04E0  FD6601          575          LD     H,[IY+1]
04E3  01FC18          576          LD     BC,-1000D
04E6  CD04F9          577          CALL   DECNO        ;GET MSD
04E9  01FF9C          578          LD     BC,-100D
04EC  CD04F9          579          CALL   DECNO
04EF  01FFF6          580          LD     BC,-10D
04F2  CD04F9          581          CALL   DECNO
04F5  DD7500          582          LD     [IX+0],L     ;STORE LSD
04F8  C9              583          RET
                      584  *
04F9  AF              585  DECNO   XOR    A
04FA  5D              586          LD     E,L
04FB  54              587          LD     D,H
04FC  3C              588          INC    A
04FD  09              589          ADD    HL,BC        ;SUBTRACT
04FE  DA04FA          590          JP     C,(DECNO+1)
0501  6B              591          LD     L,E          ;REMAINDER IN HL
0502  62              592          LD     H,D
0503  3D              593          DEC    A
0504  F5              594          PUSH   AF
0505  2010            595          JR     NZ,NOBLK
0507  3A4060          596          LD     A,[4060H]
050A  FE00            597          CP     00H
050C  2009            598          JR     NZ,NOBLK
050E  F1              599          POP    AF
050F  3E0F            600          LD     A,0FH
0511  DD7700          601          LD     [IX+0],A     ;STORE BLANK
0514  DD23            602          INC    IX
0516  C9              603          RET
0517  F1              604  NOBLK   POP    AF
0518  DD7700          605          LD     [IX+0],A     ;STORE DIGIT
051B  3E01            606          LD     A,01H
051D  324060          607          LD     [4060H],A    ;FLAG
0520  DD23            608          INC    IX
0522  C9              609          RET
                      610
                      611  *** SUBROUTINE TO DISPLAY RPM ***
0523  114004          612  DISP    LD     DE,DISBUF    ;4040
0526  0E00            613          LD     C,SEG
0528  0600            614          LD     B,00H
052A  3A4000          615          LD     A,[INBUF]
052D  CB6F            616          BIT    5,A          ;? JOG
052F  CA0545          617          JP     Z,NUMER      ;NO,JP
0532  3E0A            618          LD     A,0AH        ; "-"
0534  ED79            619          OUT    [C],A
0536  3E1A            620          LD     A,1AH        ; "-"
0538  ED79            621          OUT    [C],A
053A  3E2A            622          LD     A,2AH        ; "-"
053C  ED79            623          OUT    [C],A
053E  3E3A            624          LD     A,3AH        ; "-"
0540  ED79            625          OUT    [C],A
0542  C30551          626          JP     STEP
0545  CD0586          627  NUMER   CALL   DIGIT        ;MSD
0548  CD0586          628          CALL   DIGIT
```

FILE: TORQ4:GH          HEWLETT-PACKARD: INTRA-ARC DRIVE PROGRAM
        Fri, 23 J   1987, 18:28    PAGE  12

LOCATION OBJECT CODE LINE       SOURCE LINE

```
054B  CD0586         629            CALL    DIGIT
054E  CD0586         630            CALL    DIGIT        ;LSD
0551  CD0590         631 STEP       CALL    SCALE        ;GRAPH SIZE
0554  CD0618         632            CALL    BARG
0557  3A4003         633            LD      A,[OUTBUF]
055A  57             634            LD      D,A
055B  3A4000         635            LD      A,[INBUF]
055E  47             636            LD      B,A
055F  E683           637            AND     083H
0561  FE00           638            CP      00H          ;LO SPD ?
0563  2008           639            JR      NZ,TRES      ;NO,JP
0565  CBFA           640            SET     7,D          ;LO
0567  CBAA           641            RES     5,D
0569  CBB2           642            RES     6,D
056B  1812           643            JR      LDIT
056D  FE02           644 TRES       CP      02           ;MED SPD ?
056F  2008           645            JR      NZ,TBUR      ;NO,JP
0571  CBF2           646            SET     6,D          ;MED
0573  CBAA           647            RES     5,D
0575  CBBA           648            RES     7,D
0577  1806           649            JR      LDIT
0579  CBEA           650 TBUR       SET     5,D          ;HI
057B  CBB2           651            RES     6,D
057D  CBBA           652            RES     7,D
057F  7A             653 LDIT       LD      A,D
0580  324003         654            LD      [OUTBUF],A
0583  D360           655            OUT     [LITE],A
0585  C9             656            RET
                     657 *
0586  1A             658 DIGIT      LD      A,[DE]       ;FETCH BCD
0587  B0             659            OR      B            ;ADR MASK
0588  ED79           660            OUT     [C],A        ;WRITE
058A  13             661            INC     DE
058B  3E10           662            LD      A,10H
058D  80             663            ADD     A,B
058E  47             664            LD      B,A
058F  C9             665            RET
                     666 *
0590  3A4000         667 SCALE      LD      A,[INBUF]
0593  E683           668            AND     83H
0595  FE00           669            CP      00H          ;LO RNG ?
0597  280E           670            JR      Z,LDGLR      ;JP IF YES
0599  FE02           671            CP      02H          ;MED RNG ?
059B  2810           672            JR      Z,LDGMR      ;JP IF YES
059D  FE01           673            CP      01H          ;HI RNG ?
059F  2812           674            JR      Z,LDGHR      ;YES,JP
05A1  FD2105F8       675            LD      IY,GFR       ;* IF FULL RNG
05A5  1810           676            JR      CKOSPD
05A7  FD2105DE       677 LDGLR      LD      IY,GLR
05AB  180A           678            JR      CKOSPD
05AD  FD2105EB       679 LDGMR      LD      IY,GMR
05B1  1804           680            JR      CKOSPD
05B3  FD2105D1       681 LDGHR      LD      IY,GHR
05B7  2A4001         682 CKOSPD     LD      HL,[SPLB]    ;NEW RPM
05BA  ED5B4019       683            LD      DE,[OLDSPD]  ;OLD RPM
05BE  37             684            SCF
05BF  3F             685            CCF
```

FILE: TORQ4:GH           'LETT-PACKARD: INTRA-ARC   VE PROGRAM
            Fri, 23 J   1987, 18:28    PAGE  13

LOCATION OBJECT CODE  LINE       SOURCE LINE

```
05C0 ED52          686            SBC    HL,DE           ;SPEED CHG ?
05C2 2808          687            JR     Z,NOCHG         ;JP IF NO
05C4 2A0001        688            LD     HL,[SPLB]
05C7 224019        689            LD     [OLDSPD],HL
05CA FDE9          690            JP     [IY]
05CC 3A401B        691 NOCHG      LD     A,[OLDRDG]
05CF 5F            692            LD     E,A
05D0 C9            693            RET
05D1 1105DC        694 GHR        LD     DE,1500D        ;HI SPD
05D4 063B          695            LD     B,3BH           ;ENTER .020
05D6 DD21A3D7      696            LD     IX,0A3D7H
05DA DDE5          697            PUSH   IX
05DC 1825          698            JR     GCALC
05DE 1100EB        699 GLR        LD     DE,235D         ;LO SPD
05E1 063D          700            LD     B,3DH           ;ENTER .12
05E3 DD21F837      701            LD     IX,0F837H
05E7 DDE5          702            PUSH   IX
05E9 1818          703            JR     GCALC
05EB 1101F4        704 GMR        LD     DE,500D         ;MED SPD
05EE 063D          705            LD     B,3DH           ;ENTER .05
05F0 DD216666      706            LD     IX,06666H
05F4 DDE5          707            PUSH   IX
05F6 180B          708            JR     GCALC
05F8 1100EB        709 GFR        LD     DE,235D         ;FULL SPD
05FB 063A          710            LD     B,3AH           ;ENTER .009
05FD DD2190B7      711            LD     IX,090B7H
0601 DDE5          712            PUSH   IX
0603 37            713 GCALC      SCF
0604 3F            714            CCF
0605 ED52          715            SBC    HL,DE
0607 EB            716            EX     DE,HL
0608 CD0000        717            CALL   FLOT            ;IN C-D-E
060B E1            718            POP    HL              ;IN B-H-L
060C CD0000        719            CALL   FMPY            ;MULTIPLY
060F CD0000        720            CALL   FIXX            ;RESULT IN E
0612 1C            721            INC    E
0613 7B            722            LD     A,E
0614 32401B        723            LD     [OLDRDG],A
0617 C9            724            RET
                   725 *
0618 3A400E        726 BARG       LD     A,[GRAPH+2]
061B F5            727            PUSH   AF
061C 21400C        728            LD     HL,GRAPH
061F 3EFF          729            LD     A,0FFH          ;SEGS OFF
0621 0603          730            LD     B,03D           ;BYTE COUNTER
0623 77            731 CBR        LD     [HL],A
0624 23            732            INC    HL
0625 05            733            DEC    B
0626 20FB          734            JR     NZ,CBR
0628 21400C        735            LD     HL,GRAPH
062B 0608          736 GSEG       LD     B,08H           ;BIT COUNTER
062D 1D            737 NXT        DEC    E               ;# SEGS ON
062E FA0639        738            JP     M,SHOW
0631 CB26          739            SLA    [HL]
0633 05            740            DEC    B
0634 20F7          741            JR     NZ,NXT
0636 23            742            INC    HL              ;NEXT LOC.
```

FILE: TORQ4:GH    HEWLETT-PACKARD: INTRA-ARC DRIVE PROGRAM
       Fri, 23 J   1987, 18:29   PAGE 14

LOCATION OBJECT CODE LINE   SOURCE LINE

```
0637 18F2         743          JR      GSEG
0639 21400C       744  SHOW    LD      HL,GRAPH
063C 7E           745          LD      A,[HL]
063D D310         746          OUT     [BAR1],A
063F 23           747          INC     HL
0640 7E           748          LD      A,[HL]
0641 D320         749          OUT     [BAR2],A
0643 23           750          INC     HL
0644 7E           751          LD      A,[HL]
0645 E60F         752          AND     0FH
0647 47           753          LD      B,A
0648 F1           754          POP     AF
0649 E6F0         755          AND     0F0H
064B B0           756          OR      B
064C 32400E       757          LD      [GRAPH+2],A
064F D380         758          OUT     [BAR3],A
0651 C9           759          RET
                  760
                  761  *** SUBROUTINE FOR TIME DELAYS ***
0652 D9           762  WAIT    EXX
0653 08           763          EX      AF,AF'
0654 FDE5         764          PUSH    IY
0656 D1           765          POP     DE
0657 1B           766  LOOP    DEC     DE
0658 7A           767          LD      A,D
0659 328000       768          LD      [8000H],A
065C 326000       769          LD      [6000H],A
065F B3           770          OR      E
0660 20F5         771          JR      NZ,LOOP
0662 D9           772          EXX
0663 08           773          EX      AF,AF'
0664 C9           774          RET
                  775
                  776  *** SUBROUTINE TO START MOTOR ***
0665 2A4001       777  RUN     LD      HL,[SPLB]    ;FETCH SPEED
0668 EB           778          EX      DE,HL
0669 CD0000       779          CALL    FLOT         ;IN C-D-E
066C 3A4000       780          LD      A,[INBUF]
066F E683         781          AND     83H
0671 FE80         782          CP      80H          ;FULL SPD ?
0673 2844         783          JR      Z,CFV        ;YES,JP
0675 FE01         784          CP      01H          ;HI SPD ?
0677 282C         785          JR      Z,CBV        ;YES,JP
0679 FE02         786          CP      02H          ;MED SPD ?
067B 2814         787          JR      Z,CRV        ;YES,JP
                  788  ; shaver    Y = 0.095X-1.13
067D 063D         789          LD      B,3DH        ;ENTER 0.095
067F 21C28F       790          LD      HL,0C28FH
0682 CD0000       791          CALL    FMPY
0685 CD0000       792          CALL    FIXX         ;IN DE
0688 210001       793          LD      HL,01D
068B EB           794          EX      DE,HL
068C ED52         795          SBC     HL,DE
068E 5D           796          LD      E,L          ;RESULT IN E
068F 183A         797          JR      VCAL
                  798  ; resector  Y = .095X-1.5
0691 063D         799  CRV     LD      B,3DH        ;ENTER .095
```

```
FILE: TORQ4:GH          'LETT-PACKARD: INTRA-ARC  VE PROGRAM
           Fri, 23 J  1987, 18:29      PAGE  15

LOCATION OBJECT CODE LINE     SOURCE LINE 0693 21C28F       800            LD       HL,0C28FH
  0696 CD0000       801            CALL     FMPY
  0699 CD0000       802            CALL     FIXX          ;RESULT IN E
  069C 210001       803            LD       HL,01D
  069F EB           804            EX       DE,HL
  06A0 ED52         805            SBC      HL,DE
  06A2 5D           806            LD       E,L
  06A3 1826         807            JR       VCAL
                    808  ; burr        Y = .111X-21.5
  06A5 063D         809  CBV       LD       B,3DH         ;ENTER .111
  06A7 21E353       810            LD       HL,0E353H
  06AA CD0000       811            CALL     FMPY
  06AD CD0000       812            CALL     FIXX          ;IN E
  06B0 210016       813            LD       HL,22D
  06B3 EB           814            EX       DE,HL
  06B4 ED52         815            SBC      HL,DE
  06B6 5D           816            LD       E,L
  06B7 1812         817            JR       VCAL
                    818  ;FULL SPD RANGE V = .103X-1.73
  06B9 063D         819  CFV       LD       B,3DH         ;ENTER .103
  06BB 21D2F1       820            LD       HL,0D2F1H
  06BE CD0000       821            CALL     FMPY
  06C1 CD0000       822            CALL     FIXX          ;RESULT IN DE
  06C4 210002       823            LD       HL,02
  06C7 EB           824            EX       DE,HL
  06C8 ED52         825            SBC      HL,DE
  06CA 5D           826            LD       E,L
  06CB 3A4000       827  VCAL      LD       A,[INBUF]
  06CE CB6F         828            BIT      5,A           ;? JOG MODE
  06D0 2051         829            JR       NZ,VCM        ;JP IF YES
  06D2 CD073A       830            CALL     DIRCHG
  06D5 CBD7         831            SET      2,A           ;SET RUN
  06D7 324003       832            LD       [OUTBUF],A
  06DA D360         833            OUT      [LITE],A      ;MOTOR ON
  06DC 7B           834            LD       A,E
  06DD D330         835            OUT      [DAC],A       ;VELOCITY
  06DF 3A4000       836            LD       A,[INBUF]
  06E2 32401C       837            LD       [OLDINB],A
  06E5 CB5F         838            BIT      3,A           ;?OSC
  06E7 2809         839            JR       Z,OSC         ;YES,JP
  06E9 3A400F       840            LD       A,[FLAGS]
  06EC CB97         841            RES      2,A
  06EE 32400F       842            LD       [FLAGS],A
  06F1 C9           843            RET
  06F2 3A400F       844  OSC       LD       A,[FLAGS]
  06F5 CB57         845            BIT      2,A           ;OSC TIMER ACTV ?
  06F7 200B         846            JR       NZ,OSCTIM
  06F9 CBD7         847            SET      2,A
  06FB 32400F       848            LD       [FLAGS],A
  06FE 210055       849            LD       HL,0055H
  0701 224014       850            LD       [CTR3],HL
  0704 ED5B4014     851  OSCTIM    LD       DE,[CTR3]     ;GET COUNT
  0708 1B           852            DEC      DE
  0709 7A           853            LD       A,D
  070A B3           854            OR       E
  070B 2011         855            JR       NZ,STDAT3
  070D 3A4000       856            LD       A,[INBUF]
```

```
FILE: TORQ4:GH            'LETT-PACKARD: INTRA-ARC [  VE PROGRAM
          Fri, 23 J.  1987, 18:29      PAGE 16
LOCATION OBJECT CODE LINE      SOURCE LINE

0710 EE04           857           XOR     04H          ;FLIP FWD/REV
0712 324000         858           LD      [INBUF],A
0715 3A400F         859           LD      A,[FLAGS]
0718 CB97           860           RES     2,A
071A 32400F         861           LD      [FLAGS],A
071D C9             862           RET
071E ED534014       863 STDAT3    LD      [CTR3],DE    ;SAVE COUNT
0722 C9             864           RET
0723 3A4000         865 VCM       LD      A,[INBUF]    ;* IF JOG MODE
0726 CB67           866           BIT     4,A          ;? RUN
0728 C8             867           RET     Z
0729 3E01           868           LD      A,01H
072B D330           869           OUT     [DAC],A
072D 3A4003         870           LD      A,[OUTBUF]
0730 CBD7           871           SET     2,A          ;MOT START BIT
0732 CBCF           872           SET     1,A          ;SET FWD LITE
0734 324003         873           LD      [OUTBUF],A
0737 D360           874           OUT     [LITE],A     ;START
0739 C9             875           RET
                    876 *
073A FD2103FF       877 DIRCHG    LD      IY,03FFH
073E 214000         878           LD      HL,INBUF
0741 3A401C         879           LD      A,[OLDINB]
0744 47             880           LD      B,A
0745 3A4003         881           LD      A,[OUTBUF]
0748 CB56           882           BIT     2,[HL]       ;REV THIS TIME ?
074A 280F           883           JR      Z,REVDIR     ;JP IF YES
074C CB50           884           BIT     2,B          ;FWD LAST TIME ?
074E 2022           885           JR      NZ,SET1      ;JP IF YES
0750 CB97           886           RES     2,A          ;MOTOR OFF
0752 D360           887           OUT     [LITE],A
0754 CD0652         888           CALL    WAIT
0757 CBCF           889           SET     1,A          ;SET FWD
0759 180D           890           JR      DEL2
075B CB50           891 REVDIR    BIT     2,B          ;REV LST TIME ?
075D 2816           892           JR      Z,RES1       ;JP IF YES
075F CB97           893           RES     2,A          ;MOTOR OFF
0761 D360           894           OUT     [LITE],A
0763 CD0652         895           CALL    WAIT
0766 CB8F           896           RES     1,A          ;SET REV
0768 D360           897 DEL2      OUT     [LITE],A
076A FD210010       898           LD      IY,0010H
076E CD0652         899           CALL    WAIT
0771 C9             900           RET
0772 CBCF           901 SET1      SET     1,A          ;FWD DIR
0774 C9             902           RET
0775 CB8F           903 RES1      RES     1,A          ;REV DIR
0777 C9             904           RET
                    905 *
                    906 *** SUBROUTINE TO TEST LITES AND DIGITS ***
0778 328000         907 CHECK     LD      [8000H],A
077B 326000         908           LD      [6000H],A
077E 3E0C           909           LD      A,0CH
0780 324000         910           LD      [INBUF],A
0783 3EEB           911           LD      A,235D
0785 324001         912           LD      [SPLB],A
0788 AF             913           XOR     A
```

FILE: TORQ4:GH          'LETT-PACKARD: INTRA-ARC   VE PROGRAM
               Fri, 23 J. 1987, 18:29     PAGE  17

LOCATION OBJECT CODE LINE     SOURCE LINE

```
0789 324002       914        LD      [SPHB],A
078C 3E08         915        LD      A,08H
078E D360         916        OUT     [LITE],A
0790 3E2F         917        LD      A,02FH
0792 32400E       918        LD      [GRAPH+2],A
0795 D380         919        OUT     [BAR3],A
0797 3E0F         920        LD      A,0FH
0799 CD087A       921        CALL    DIGOUT
079C 114004       922        LD      DE,DISBUF
079F CD015C       923        CALL    DIGITS
07A2 1E00         924        LD      E,00H
07A4 CD0618       925        CALL    BARG
07A7 CD0867       926        CALL    DELAY
07AA 3E06         927        LD      A,REVLEV
07AC 324007       928        LD      [DISBUF+3],A
07AF CD087D       929        CALL    (DIGOUT+3)
07B2 CD0867       930        CALL    DELAY
07B5 CD0867       931        CALL    DELAY
07B8 CD0867       932        CALL    DELAY
07BB CD0867       933        CALL    DELAY
07BE 3E08         934        LD      A,08H
07C0 CD087A       935        CALL    DIGOUT
07C3 CD0867       936        CALL    DELAY
07C6 3E0F         937        LD      A,0FH           ;BLANKS TO DISPLAY
07C8 CD087A       938        CALL    DIGOUT
07CB 3E08         939        LD      A,08H           ;8'S TO DSPLY BUF
07CD CD086F       940        CALL    FILBUF
07D0 0E90         941        LD      C,SEG2          ;8'S IN RPM LO
07D2 0640         942        LD      B,40H
07D4 210004       943        LD      HL,04H
07D7 114004       944        LD      DE,DISBUF
07DA CD0163       945        CALL    NXTDIG
07DD CD0867       946        CALL    DELAY
07E0 3E0F         947        LD      A,0FH           ;BLANK RPM LO
07E2 CD086F       948        CALL    FILBUF
07E5 0E90         949        LD      C,SEG2
07E7 0640         950        LD      B,040H
07E9 210004       951        LD      HL,04H
07EC 114004       952        LD      DE,DISBUF
07EF CD0163       953        CALL    NXTDIG
07F2 1E14         954        LD      E,20D           ;DSPLY BAR GRAPH
07F4 CD0618       955        CALL    BARG
07F7 CD0867       956        CALL    DELAY
07FA 1E00         957        LD      E,00H
07FC CD0618       958        CALL    BARG
07FF 3E08         959        LD      A,08H           ;8'S TO DSPLY BUF
0801 CD086F       960        CALL    FILBUF
0804 0E90         961        LD      C,SEG2          ,8'S TO RPM HI
0806 0600         962        LD      B,00H
0808 210004       963        LD      HL,04H
080B 114004       964        LD      DE,DISBUF
080E CD0163       965        CALL    NXTDIG
0811 CD0867       966        CALL    DELAY
0814 3E0F         967        LD      A,0FH           ;BLANK DSPLY BUF
0816 CD086F       968        CALL    FILBUF
0819 0E90         969        LD      C,SEG2
081B 0600         970        LD      B,00H
```

```
FILE: TORQ4:GH        HEWLETT-PACKARD: INTRA-ARC DRIVE PROGRAM
         Fri, 23 J  1987, 18:29      PAGE   18
LOCATION OBJECT CODE LINE     SOURCE LINE 081D 210004         971           LD    HL,04H
   0820 114004         972           LD    DE,DISBUF
   0823 CD0163         973           CALL  NXTDIG
   0826 3E88           974           LD    A,88H       ;DSPLY LO
   0828 D360           975           OUT   [LITE],A
   082A CD0867         976           CALL  DELAY
   082D 3E48           977           LD    A,48H       ;DSPLY MED
   082F D360           978           OUT   [LITE],A
   0831 CD0867         979           CALL  DELAY
   0834 3E28           980           LD    A,28H       ;DSPLY HI
   0836 D360           981           OUT   [LITE],A
   0838 CD0867         982           CALL  DELAY
   083B 3E0A           983           LD    A,0AH       ;DSPLY FWD
   083D D360           984           OUT   [LITE],A
   083F CD0867         985           CALL  DELAY
   0842 3E1A           986           LD    A,1AH       ;DSPLY FTSW
   0844 D360           987           OUT   [LITE],A
   0846 CD0867         988           CALL  DELAY
   0849 3E1F           989           LD    A,01FH
   084B D380           990           OUT   [BAR3],A    ;DSPLY NORM & CONT
   084D CD0867         991           CALL  DELAY
   0850 3E02           992           LD    A,02H
   0852 D360           993           OUT   [LITE],A    ;AUDIO ON
   0854 CD0867         994           CALL  DELAY
   0857 3E0A           995           LD    A,0AH       ;AUDIO OFF
   0859 D360           996           OUT   [LITE],A
   085B 110891         997           LD    DE,LORNG
   085E CD015C         998           CALL  DIGITS
   0861 3E8A           999           LD    A,08AH
   0863 324003        1000           LD    [OUTBUF],A
   0866 C9            1001           RET
                      1002 *
   0867 FD217FFF      1003 DELAY     LD    IY,07FFFH
   086B CD0652        1004           CALL  WAIT
   086E C9            1005           RET
                      1006 *
   086F 214004        1007 FILBUF    LD    HL,DISBUF
   0872 0609          1008           LD    B,09D
   0874 05            1009 SEV       DEC   B
   0875 C8            1010           RET   Z
   0876 77            1011           LD    [HL],A
   0877 23            1012           INC   HL
   0878 18FA          1013           JR    SEV
                      1014 *
   087A CD086F        1015 DIGOUT    CALL  FILBUF
   087D 114004        1016           LD    DE,DISBUF
   0880 0E00          1017           LD    C,SEG
   0882 0600          1018           LD    B,00H
   0884 CD0586        1019           CALL  DIGIT
   0887 CD0586        1020           CALL  DIGIT
   088A CD0586        1021           CALL  DIGIT
   088D CD0586        1022           CALL  DIGIT
   0890 C9            1023           RET
                      1024 *
                      1025 *DATA CONSTANTS
                      1026 *
   0891 0F            1027 LORNG     DEFB  0FH
```

```
FILE: TORQ4:GH            LETT-PACKARD: INTRA-ARC   VE PROGRAM
         Fri, 23 J  1987, 18:29      PAGE  19

LOCATION OBJECT CODE LINE      SOURCE LINE 0892 04            1028             DEFB    04H
  0893 00            1029             DEFB    00H
  0894 00            1030             DEFB    00H
  0895 05            1031             DEFB    05H
  0896 03            1032             DEFB    03H
  0897 02            1033             DEFB    02H
  0898 0F            1034             DEFB    0FH
  0899 0F            1035 MIDRNG      DEFB    0FH
  089A 09            1036             DEFB    09H
  089B 00            1037             DEFB    00H
  089C 00            1038             DEFB    00H
  089D 00            1039             DEFB    00H
  089E 00            1040             DEFB    00H
  089F 05            1041             DEFB    05H
  08A0 0F            1042             DEFB    0FH
  08A1 02            1043 HIRNG       DEFB    02H
  08A2 05            1044             DEFB    05H
  08A3 00            1045             DEFB    00H
  08A4 00            1046             DEFB    00H
  08A5 00            1047             DEFB    00H
  08A6 00            1048             DEFB    00H
  08A7 05            1049             DEFB    05H
  08A8 01            1050             DEFB    01H
  08A9 02            1051 FULRNG      DEFB    02H
  08AA 05            1052             DEFB    05H
  08AB 00            1053             DEFB    00H
  08AC 00            1054             DEFB    00H
  08AD 05            1055             DEFB    05H
  08AE 03            1056             DEFB    03H
  08AF 02            1057             DEFB    02H
  08B0 0F            1058             DEFB    0FH
                     1059 *
                     1060 *DEFINED STORAGE AREAS
                     1061 *
                     1062             ORG     4000H
  4000               1063 INBUF       DEFS    1D
  4001               1064 SPLB        DEFS    1D
  4002               1065 SPHB        DEFS    1D
  4003               1066 OUTBUF      DEFS    1D
  4004               1067 DISBUF      DEFS    8D
  400C               1068 GRAPH       DEFS    3D
  400F               1069 FLAGS       DEFS    1D
  4010               1070 CTR1        DEFS    2D
  4012               1071 CTR2        DEFS    2D
  4014               1072 CTR3        DEFS    2D
  4016               1073 CTR4        DEFS    1D
  4017               1074 CTR5        DEFS    2D
  4019               1075 OLDSPD      DEFS    2D
  401B               1076 OLDRDG      DEFS    1D
  401C               1077 OLDINB      DEFS    1D

Errors=    0
```

What is claimed is:

1. A disposable, limited use cutting blade assembly for use with a handpiece having motor means for rotatably driving said cutting blade assembly, the handpiece having bore means for receiving the cutting blade assembly and sensing means disposed adjacent said bore means for sensing a coded representation of a predetermined characteristic of the cutting blade assembly to control an operating parameter of said motor, said cutting blade assembly comprising:

an elongate tubular outer member having a distal end with an opening therein, a proximal end, a plastic hub unremovably secured to said proximal end so as to be a permanent part of said outer member, said hub being configured to be directly received and engaged in said handpiece bore means in a particular orientation relative to the sensing means, and having a coding structure in said hub for identifying the predetermined characteristic of the cutting blade to be sensed by the sensing means; and an elongate inner member received in said outer member and having a distal cutting end disposed adjacent said opening in said distal end of said outer member, and a proximal end adapted to be received in the handpiece bore means and rotatably driven by the motor means to rotate said inner member in said outer member.

2. The assembly of claim 1 further comprising at least one coding element, wherein said hub includes a locator on said hub for defining a single angular orientation of said hub relative to said handpiece in which said hub can be received in said handpiece bore means, and wherein said coding structure is located at a predetermined angular location in said hub relative to said single angular orientation, wherein presence and absence of said coding element as part of said coding structure at said angular location identify said predetermined characteristic of said cutting blade assembly to said sensing means.

3. The assembly of claim 1 further comprising plural coding elements, wherein said hub includes a locator for defining a single angular orientation of said hub relative to said handpiece in which said hub can be received in said handpiece bore means, and wherein said coding structure is located at plural predetermined angular locations in said hub relative to said single angular orientation, wherein presence and absence of said coding elements as part of said coding structure at said angular locations identify said predetermined characteristic of said cutting blade assembly to said sensing means.

4. The assembly of claim 3 wherein said locator is a locator key projecting radially from said hub at a prescribed circumferential location to be received in the handpiece bore means only in a single angular orientation of said hub relative to said handpiece.

5. The assembly of claim 3 wherein said coding elements are permanent magnets.

6. The assembly of claim 1 wherein said hub has a proximal end and further includes:

a forward hollow cylindrical section;

a proximal hollow cylindrical section disposed at said proximal end of said hub; and an intermediate hollow cylindrical section disposed longitudinally between said forward and proximal sections and having a smaller outside diameter than said forward and proximal sections;

wherein said coding structure is spaced forwardly from said proximal end of said hub.

7. The assembly of claim 6 wherein said coding structure is spaced forwardly of said proximal section of said hub.

8. The assembly of claim 6 further comprising plural coding elements, wherein said hub includes a locator for defining a single angular orientation of said hub relative to said handpiece in which said hub can be received in said handpiece bore means, and wherein said coding structure is located at plural predetermined angular locations in said hub relative to said single angular orientation, wherein presence and absence of said coding elements as part of said coding structure at said angular locations identifies said predetermined characteristic of said cutting blade assembly to said sensing means.

9. The assembly of claim 8 wherein said outer member has a longitudinal axis, and wherein said hub includes a surface disposed interiorly within said hub in a plane substantially perpendicular to said longitudinal axis, wherein said coding structure includes plural recesses defined in said surface at said plural predetermined angular locations, respectively, for receiving said coding elements.

10. The assembly of claim 8 wherein the predetermined characteristic of said cutting blade is the type of cutting end of said inner member, and wherein the operating parameter of the motor means is a range of speeds at which said inner member is rotatably driven by the motor means.

11. The assembly of claim 6 further comprising at least one coding element, wherein said hub includes a locator on said hub for defining a single angular orientation of said hub relative to said handpiece in which said hub can be received in said handpiece bore means, and wherein said coding structure is located at a predetermined angular location in said hub relative to said single angular orientation, wherein presence and absence of said coding element as part of said coding structure at said angular location identifies said predetermined characteristic of said cutting blade assembly to said sensing means.

12. The assembly of claim 11 wherein said outer member has a longitudinal axis, and wherein said hub includes a surface disposed interiorly within said hub in a plane substantially perpendicular to said longitudinal axis, wherein said coding structure includes at least one recess defined in said surface at said predetermined angular location for receiving said coding element.

13. The assembly of claim 11 wherein the predetermined characteristic of said cutting blade is the type of cutting end of said inner member, and wherein the operating parameter of the motor means is a range of speeds at which said inner member is rotatably driven by the motor means.

14. A disposable, limited use cutting blade assembly for utilization with a handpiece having motor means for rotatably driving different types of cutting blade assemblies over different respective ranges of rotating speeds, handpiece bore means for receiving the cutting blade assembly, and sensing means disposed adjacent the bore means for sensing a coded representation of the type of cutting blade assembly received in the bore, said assembly comprising:

an elongate tubular outer member having a distal end with an opening therein and a proximal end, said outer member having a plastic hub unremovably secured to said proximal end to comprise a permanent part of said outer member, said hub being configured to be directly inserted into the bore means of the handpiece in a particular orientation relative to said sensing means, said hub including coding structure at one of plural possible coding locations to be sensed by the sensing means when said hub is received in the handpiece bore means in said particular orientation, wherein the coding location of said coding structure is sensed by said sensing means to identify the type of said cutting blade assembly; and an elongate inner member received in said outer member and having a distal cutting end disposed adjacent said opening in said distal end of said outer member, said inner member having a proximal end configured to be received in the bore means of the handpiece and to be rotatably driven by the motor means to rotate in said outer member.

15. The assembly of claim 14 further comprising at least one coding element, wherein presence and absence of said coding element at said coding locations identify the type of said cutting blade assembly.

16. The assembly of claim 15 wherein said coding structure in said hub includes a recess defined interiorly within said hub at said coding location for alternatively receiving and not receiving said coding element.

17. The assembly of claim 14 wherein said hub has a proximal end and includes:

a forward hollow cylindrical section;

a proximal hollow cylindrical section disposed at a proximal end of said hub; and an intermediate hollow cylindrical section disposed longitudinally between said forward and proximal sections and having a smaller outside diameter than said forward and proximal sections;

wherein said coding structure is spaced longitudinally forward from said proximal end of said hub.

18. The assembly according to claim 17 further comprising two coding elements, wherein said hub includes at least two recesses defined interiorly within said hub at two respective coding locations for alternatively receiving and not receiving said coding elements.

19. The assembly of claim 17 further comprising at least one coding element, wherein presence and absence of said coding element at said coding locations identify the type of said cutting blade assembly.

20. The assembly of claim 19 wherein said coding element is a permanent magnet.

21. The assembly of claim 19 wherein said coding structure in said hub includes a recess defined interiorly within said hub at said coding location for alternatively receiving and not receiving said coding element.

22. A disposable, limited use cutting blade assembly for use with a handpiece having motor means for rotatably driving said cutting blade assembly, bore means for receiving said cutting blade assembly and sensing means disposed adjacent said bore means, said cutting blade assembly comprising:

an elongate tubular outer member having a distal end with an opening therein and a proximal end;

an elongate inner member received in said outer member and having a distal cutting end disposed adjacent said opening in said distal end of said outer member and a proximal end adapted to be received in the bore means of the handpiece and to be rotatably driven by the motor means to rotate in said outer member;

a plastic hub unremovably mounted on said proximal end of said outer member and having a configuration to be directly received in the bore means of the handpiece in a particular orientation relative to the sensing means; and coding means having a characteristic detectable by said sensing means, said coding means being received by said plastic hub so that said cutting blade assembly can be identified by the sensing means in the handpiece detecting the presence of said coding means.

23. The method of identifying to a handpiece of a rotatable blade surgical instrument a type of cutting blade assembly removably inserted into the handpiece, wherein the handpiece includes a sensor for detecting a coded representation of the type of cutting blade assembly inserted into the handpiece, said method comprising the step of coding the cutting blade assembly itself, as opposed to employing a separate coding adapter secured between the cutting blade assembly and the handpiece, to provide the coded representation of the type of cutting blade assembly inserted into the handpiece.

24. The method of claim 23 wherein the step of coding includes alternatively disposing and not disposing coding elements at plural specified coding locations in said cutting blade assembly for detection by said sensor of the presence and absence of said coding elements at said coding locations to identify the type of cutting blade assembly inserted into the handpiece.

* * * * *